United States Patent [19]

Bloom et al.

[11] Patent Number: 5,106,867

[45] Date of Patent: Apr. 21, 1992

[54] METHOD OF INCREASING LEAN MEAT IN EDIBLE ANIMALS

[75] Inventors: Jonathan D. Bloom, Hartsdale, N.Y.; Thomas H. Claus, Montvale; Vern G. DeVries, Ridgewood, both of N.J.; Jo A. Dolan, Spring Valley; Minu D. Dutia, West Nyack, both of N.Y.

[73] Assignee: American Cyanamid Company, Stamford, Conn.

[21] Appl. No.: 679,313

[22] Filed: Apr. 5, 1991

Related U.S. Application Data

[63] Continuation-in-part of Ser. No. 519,192, May 4, 1990.

[51] Int. Cl.$^5$ .......................................... A61K 31/335
[52] U.S. Cl. .................................. 514/465; 514/376; 548/229; 549/434; 549/437
[58] Field of Search ................. 514/465; 549/434, 437

[56] References Cited

U.S. PATENT DOCUMENTS

| | | | |
|---|---|---|---|
| 4,016,284 | 4/1977 | Van Hoof | 514/465 |
| 4,032,575 | 6/1977 | Ikezaki et al. | 564/363 |
| 4,276,304 | 6/1981 | Ikezaki et al. | 564/363 |
| 4,287,205 | 9/1981 | Szent-Gyorgii | 549/435 |
| 4,309,443 | 1/1982 | Smith et al. | 564/165 |
| 4,338,333 | 7/1982 | Ainsworth et al. | 564/165 |
| 4,341,793 | 7/1982 | Ferris | 549/467 |
| 4,374,149 | 2/1983 | Philion | 564/363 |
| 4,382,958 | 5/1983 | Duckworth | 564/363 |
| 4,385,066 | 5/1983 | Ainsworth et al. | 560/42 |
| 4,396,627 | 8/1983 | Ainsworth et al. | 564/363 |
| 4,404,222 | 9/1983 | Baker et al. | 514/238.8 |
| 4,407,819 | 10/1983 | Kiernan et al. | |
| 4,432,993 | 2/1984 | Ferris | 549/467 |
| 4,452,816 | 6/1984 | Philion | 514/465 |
| 4,478,849 | 10/1984 | Ainsworth et al. | 564/165 |
| 4,490,392 | 12/1984 | Ikezaki et al. | 564/363 |
| 4,654,371 | 3/1987 | Ainsworth et al. | 514/555 |
| 4,751,246 | 6/1988 | Philion | 514/649 |
| 4,753,962 | 6/1988 | Ainsworth et al. | 514/538 |
| 4,772,631 | 9/1988 | Holloway et al. | 514/539 |

FOREIGN PATENT DOCUMENTS 0159936 5/1972 Australia ........................... 549/435

Primary Examiner—Donald G. Daus
Attorney, Agent, or Firm—H. G. Jackson

[57] ABSTRACT

The present invention discloses substituted 1,3-benzodioxoles which possess anti-diabetic and/or anti-hyperglycemic and/or anti-obesity properties in humans and other animals.

6 Claims, 2 Drawing Sheets

METHOD OF INCREASING LEAN MEAT IN EDIBLE ANIMALS

This is Continuation-in-Part Application of copending U.S. Pat. application Ser. No. 07/519,192 filed May 4, 1990.

The present invention relates to novel 1,3-benzodioxole compounds which have antidiabetic and/or antihyperglycemic properties in mammals. More particularly it relates to novel substituted 5-(2-((2-aryl-2-hydroxyethyl)amino)propyl)-1,3-benzodioxoles. The present invention also relates to pharmaceutical compositions comprising these compounds, methods for the preparation of these compounds, as well as methods for the use of these compounds in treating diabetes and/or hyperglycemia and/or obesity in mammals.

BACKGROUND OF THE INVENTION

It is well known to employ medicinal agents in the treatment of persons suffering from diabetes, hyperglycemia and obesity.

Ainsworth et al, U.S. Pat. No. 4,478,849, disclose secondary amine compounds having the general formula (I):

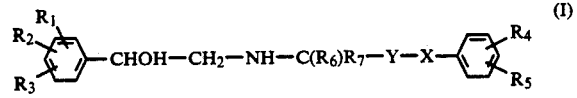

wherein $R_1$ is a hydrogen, fluorine or chlorine atom or a hydroxyl, hydroxymethyl, methyl, methoxyl, amido, formamido, acetamido, methylsulfonylamido, nitro, benzyloxy, methylsulfonylmethyl, ureido, trifluoromethyl, or methoxybenzylamino group; $R_2$ is a hydrogen, fluorine or chlorine atom or a hydroxyl group; $R_3$ is a hydrogen or chlorine atom or a hydroxyl group; $R_4$ is a carboxylic group or a salt, ester or amide thereof; $R_5$ is a hydrogen, chlorine or fluorine atom or a methyl, methoxyl, or hydroxyl group or a carboxylic acid group or a salt, ester or amide thereof; $R_6$ is a hydrogen atom or a methyl or propyl group; X is an oxygen atom or a bond; and Y is an alkylene group of up to 6 carbon atoms or a bond, which have anti-obesity and/or antihyperglycemic activity.

Ainsworth et al, U.S. Pat. No. 4,396,627, disclose secondary amine compounds of the formula (II):

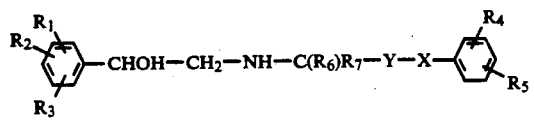

wherein $R_1$, $R_2$ and $R_3$ are as defined in relation to formula (I) or each independently represents a bromine atom; $R_4$ is an alkyl group of 1 to 10 carbon atoms substituted by a hydroxyl, lower alkoxyl, oxo, lower acyloxy or $OCH_2CO_2H$ group or lower alkyl ester thereof; $R_5$ is a hydrogen, chlorine or fluorine atom or a methyl, methoxyl or hydroxyl group or a carboxylic acid group or a salt, ester or amide thereof; $R_6$ is a hydrogen atom or a methyl, ethyl or propyl group; $R_7$ is a hydrogen atom or a methyl, ethyl, or propyl group; X is an oxygen atom or a bond; and Y is an alkylene group of up to six carbon atoms or a bond; which are useful in reducing high blood glucose and lipid levels in humans and animals.

Ainsworth et al, U.S. Pat. No. 4,385,066 disclose arylethanol amine derivatives of the formula (III):

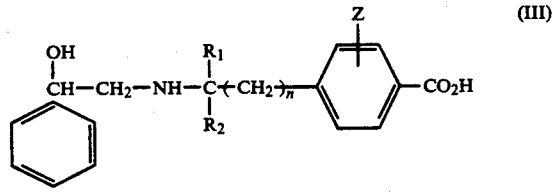

wherein $R_1$ and $R_2$ are hydrogen or methyl; n is 1, 2 or 3; and Z is alkyl of 1 to 6 carbon atoms, alkoxy of 1 to 6 carbon atoms, halogen or hydrogen; useful in treating obesity and/or hyperglycemia and/or inflammation in mammals.

Ferris, U.S. Pat. No. 4,341,793 discloses secondary amine compounds of the formula (IV):

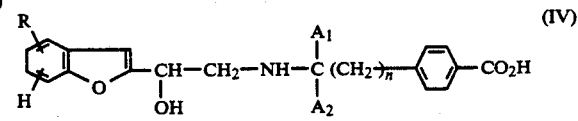

wherein $A_1$ and $A_2$ are hydrogen or methyl; n is 1, 2 or 3; and R is hydrogen, chlorine, bromine, hydroxy, nitro, amino or trifluoromethyl; which are useful as anti-hyperglycemia agents or anti-obesity agents.

Smith et al., U.S. Pat. No. 4,309,443, disclose cinnamic acid derivatives of the formula (V):

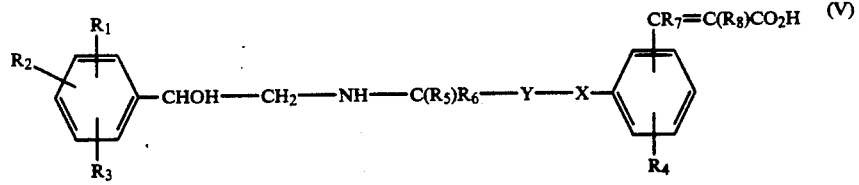

wherein $R_1$ and $R_2$ and $R_3$ are as defined in relation to formula (II); $R_4$ is a hydrogen, chlorine or fluorine atom or a methyl, methoxyl or hydroxyl group or a carboxylic acid group or a salt, ester or amide thereof; $R_5$ and $R_6$ are a hydrogen atom or methyl group; $R_7$ and $R_8$ are a hydrogen atom or methyl or ethyl group; X is an oxygen atom or a bond; and Y is an alkylene group of up to 5 carbon atoms; which have been found to possess anti-obesity and/or anti-hyperglycemia activity.

Duckworth, U.S. Pat. No. 4,382,958, disclose secondary amine compositions of the formula (VI):

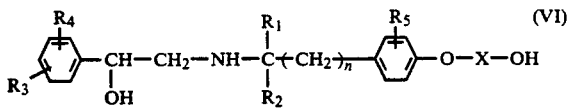

wherein each of $R_1$ and $R_2$ are hydrogen, methyl or ethyl; $R_3$ is hydrogen, fluorine, chlorine, bromine or trifluoromethyl; each of $R_4$ and $R_5$ is hydrogen, fluorine, chlorine, bromine, alkyl having 1 to 6 carbon atoms, or alkoxy having 1 to 6 carbon atoms; n is 1 or 2; and X is straight or branched alkylene having 1 to 12 carbon atoms; which are anti-obesity, hypoglycemia, anti-inflammatory and platelet aggregation inhibiting agents.

Ainsworth et al., U.S. Pat. No. 4,654,371, disclose secondary amine compounds of the formula (VII):

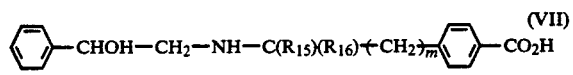

wherein $R_{15}$ is a hydrogen atom or a methyl group; $R_{16}$ is a hydrogen atom or a methyl group and m is 1; useful in treating obesity and hyperglycemia in humans or animals Ikezaki et al., U.S. Pat. No. 4,490,392 disclose benzylalcohol derivatives of the formula (VIII):

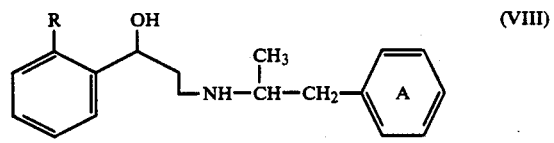

wherein R is hydroxy, benzyloxy, halogen or alkoxy having 1 to 4 carbon atoms and Ring A is monomethoxyphenyl, dimethoxyphenyl, trimethoxyphenyl or 3,4-methylenedioxyphenyl; which are useful as anti-diabetic agents.

Ferris, U.S. Pat. No 4,432,993 discloses 2-(2-benzofuranyl)ethanolamine derivatives of the formula (IX):

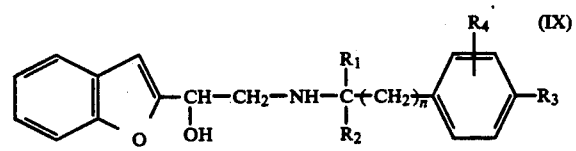

wherein $R_1$ is hydrogen or methyl; $R_2$ is hydrogen or methyl; $R_3$ is hydroxy, hydroxy($C_1$-$C_6$)alkoxy, benzyloxy or a group X-Y-Z wherein (i) X is a bond or oxygen, Y is a $C_1$-$C_6$ straight or branched alkylene, and Z is hydrogen or carboxy; or (ii) X is a bond or —O—$CH_2$—, Y is a $C_2$-$C_6$ straight or branched alkenylene and Z is carboxy; $R_4$ is hydrogen, hydroxy, halogen, $C_1$-$C_6$ alkyl or $C_1$-$C_6$ alkoxy; and n is 1, 2 or 3; which have anti-obesity, hypoglycemia, anti-inflammatory, and platelet-aggregation inhibiting activity.

Ainsworth et al., U.S. Pat. No. 4,338,333 disclose ethanamine derivatives of the formula (X):

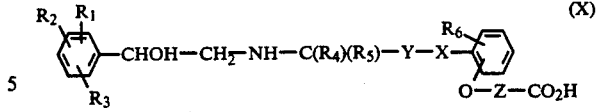

wherein $R_1$, $R_2$ and $R_3$ are as defined in relation to formula (I) or each independently represent a bromine atom; $R_4$ is a hydrogen atom or methyl group; $R_5$ is a hydrogen atom or methyl group; $R_6$ is a hydrogen, fluorine or chlorine atom or a methyl, methoxyl or hydroxy group; X is an oxygen atom or a bond; Y is an alkylene group of up to 6 carbon atoms or a bond; and Z is an alkylene, alkenylene or an alkynylene group of up to 10 carbon atoms; which possess anti-obesity and anti-hyperglycemia properties.

Ikezaki et al., U.S. Pat. No. 4,032,575 disclose benzylalcohol amine derivatives of the formula (XI):

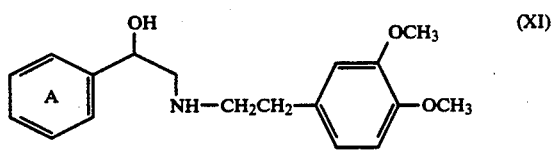

wherein Ring A is monohydroxyphenyl; which induce a decrease in blood sugar levels when Ring A is 2-hydroxyphenyl.

Holloway et al., U.S. Pat. No. 4,772,631, disclose phenoxyacetic acid ethers of the formula (XII):

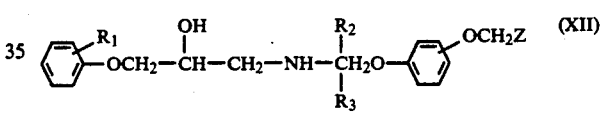

wherein $R_1$ or fluorine; $R_2$ and $R_3$ are hydrogen or alkyl having 1 to 3 carbon atoms; Z is $CH_2OH$ or a group —$COR_4$ in which $R_4$ is OH, $NH_2$ or alkoxy having 1 to 6 carbon atoms; which are useful in treating obesity and related conditions.

Philion, U.S. Pat. No. 4,751,246 disclose benzenemethanol and ethylamine compounds of the formula (XIII):

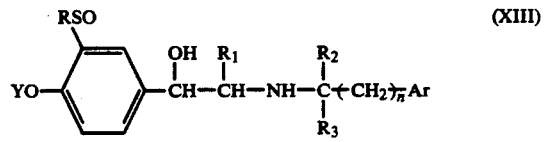

wherein $R_1$, $R_2$ and $R_3$ are independently hydrogen or lower alkyl; n is an integer from 1 to 3; Ar is phenyl, methylenedioxyphenyl or phenyl having from 1 to 3 substituents selected from the group consisting of halo, lower alkyl, hydroxy and lower alkoxy; R is lower alkyl; and Y is hydrogen, lower alkyl, lower alkoxy, lower alkyl; lower alkanoyl, aroyl, benzenesulfonyl or toluenesulfonyl; which are useful as anti-hypertensive agents.

It has now been discovered that a group of novel substituted 5-(2-((2-aryl-2-hydroxyethyl)amino) propyl)-1,3-benzodioxoles possess vastly increased anti-hyperglycemia and anti-obesity properties with greater $\beta_3$ selectivity in comparison with the prior art compounds. The compounds are therefore useful in treating diabetes, hyperglycemia and obesity, exhibiting minimal side effects, i.e. heart rate increase and muscle tremor in humans and animals, when formulated into pharmaceutical compositions.

SUMMARY OF THE INVENTION

Figure 1:
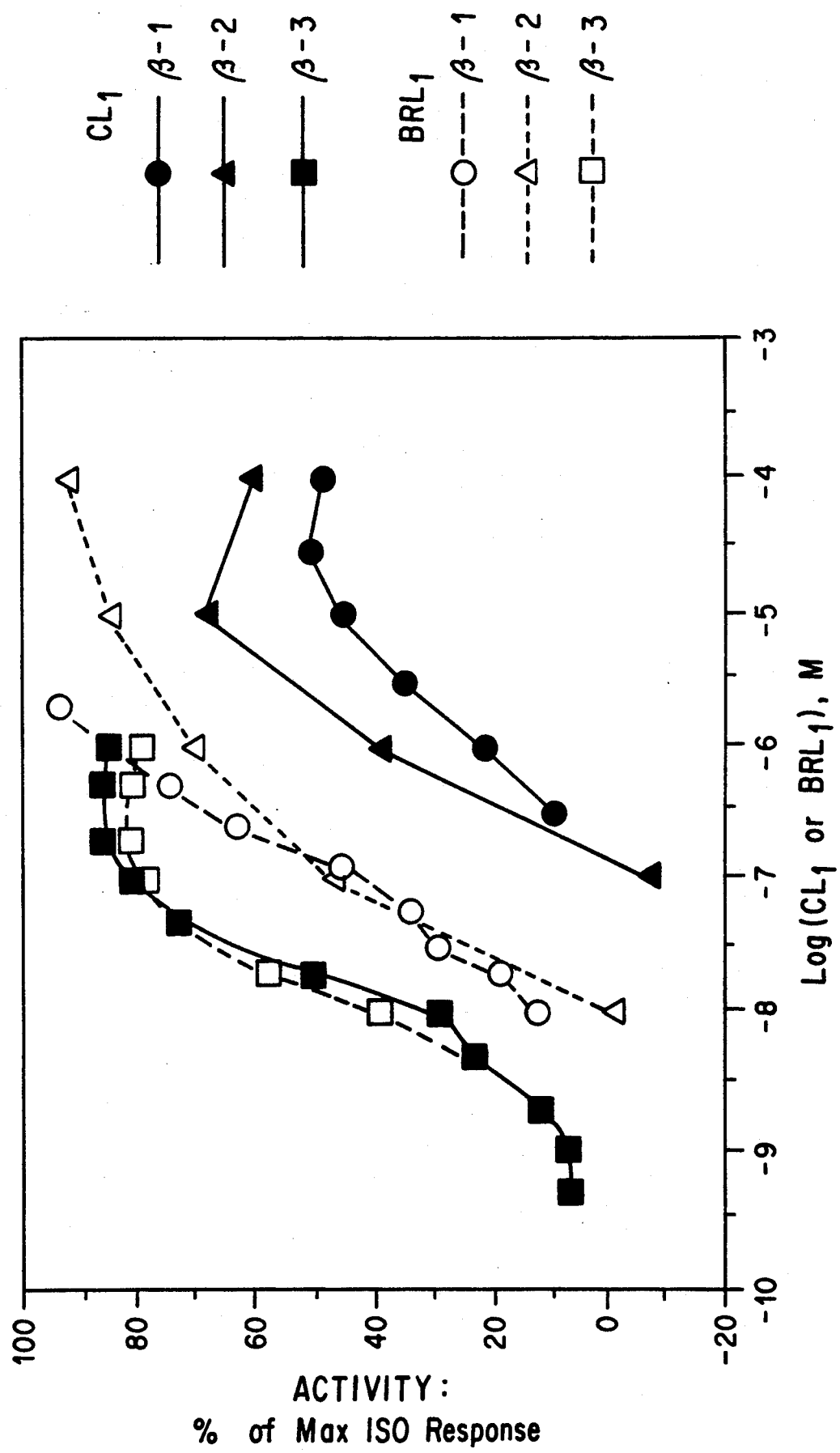
FIG. 1 shows a comparison of the selectivity between a compound of the present invention and a prior art compound

According to the present invention there are provided new compounds of the formula (XIV):

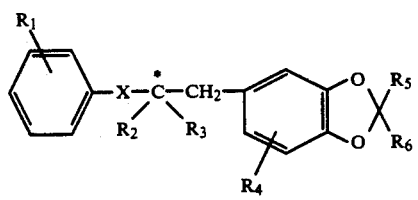

wherein $R_1$ and $R_4$ may be one or more groups which may be the same or different and are selected from the group consisting of hydrogen, $C_1$ to $C_4$ alkyl, $C_1$ to $C_4$ alkoxy, hydroxy, halogen, trifluoromethyl, carboxy, hydroxyalkyl, alkoxycarbonyl, $C_1$ to $C_4$ thioalkyl, sulfonyl and sulfinyl; X is a divalent radical consisting of

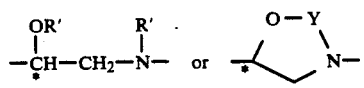

wherein R' is selected from the group consisting of hydrogen, $C_1$ to $C_4$ alkyl and $C_1$ to $C_4$ acyl and Y is selected from the group consisting of carbonyl and thiocarbonyl; $R_2$ and $R_3$ may be the same or different and are selected from the group consisting of hydrogen and $C_1$ to $C_4$ alkyl; $R_5$ and $R_6$ are selected from the group consisting of hydrogen, carboxy, alkoxycarbonyl, hydroxymethyl, $-CH_2OCH_2COOR_7$ and $-CH_2OCH_2CH_2OR_7$, where $R_7$ is hydrogen or $C_1$ to $C_4$ alkyl; with the provision that $R_5$ and $R_6$ may not both be hydrogen; and the pharmaceutically acceptable salts and esters thereof, the enantiomers thereof, the racemic mixtures thereof and the diastereomeric mixtures thereof.

The compounds of the above formula have centers of asymmetry at the carbon atoms marked with an asterisk. The compounds may, therefore, exist in at least two and often four stereoisomeric forms. The present invention encompasses all stereoisomers of the compounds whether free from other stereoisomers or admixed with other stereoisomers in any proportion and thus includes, for instance, racemic mixture of enantiomers as well as the diastereomeric mixture of isomers.

A preferred embodiment of the invention is compounds wherein $R_1$ is one or two groups as defined above. A more preferred embodiment is compounds wherein $R_1$ is two of the defined groups.

Preferably both asymmetric carbon atoms have the R absolute stereochemical configuration.

The absolute configuration of any compound may be determined by conventional X-ray cyrstallography.

The preferred compounds are (R*,R*)-(+/−)-5-(2-((2-(3-chlorophenyl)-2-hydroxyethyl)amino)propyl)-1,3-benzodioxole-2,2-dicarboxylic acid, dimethyl ester; (R*,R*)-(+/−)-5-(2-((2-(3-chlorophenyl)-2-hydroxyethyl)-amino)propyl)-1,3-benzodioxole-2,2-dicarboxylic acid, diethyl ester; (R*,R*)-(+/−)-5-(2-((2-(3-chlorophenyl)-2-hydroxyethyl)amino)propyl)-1,3-benzodioxole-2,2-dicarboxylic acid, diisopropyl ester; (R*,R*)-(+/−)-5-(2-((2-(3-chlorophenyl)-2-hydroxyethyl)amino)propyl)-1,3-benzodioxole-2,2-dicarboxylic acid, disodium salt; (R*,R*)-(+/−)((5-(2-(5-(3-chlorophenyl)-2-oxo-3-oxazolidinyl)propyl)-1,3-benzodioxole-2,2-diyl)-bis-(methyleneoxy)bis acetic acid, dimethyl ester; (R*,R*)-(+/−)-3-(2-(2,2-bis(2-hydroxyethoxy)methyl)-1,3-benzodioxole-5-yl)-1-methylethyl)5-(3-chlorophenyl)-2-oxazolidinone; (R*,R*)-(+/−)-((5-(2-((2-(3-chlorophenyl)-2-hydroxyethyl) amino)-propyl)-1,3-benzodioxole-2,2-diyl)bis(methyleneoxy)) bis acetic acid, dimethyl ester; (R*,R*)-(+/−)alpha-(((2-(2,2-bis(2-hydroxyethoxyl)methyl)-1,3-benzodioxole-5-yl)-1-methylethyl)amino)methyl)-3-chlorobenzenemethanol; and the optically active derivatives thereof.

Also according to the present invention there is provided a method of treating diabetes and/or hyperglycemia and/or obesity in humans or other mammals which comprises administering to a human or other mammal an antiobesity effective amount or an anti-hyperglycemia effective amount of a compound of the present invention.

Further, according to the present invention there are provided pharmaceutical compositions of matter comprising an effective amount of the compounds of the present invention in combination with a pharmaceutically acceptable carrier; as well as a method for increasing the content of lean meat in edible mammals, which comprises administering to edible mammals an effective amount of the compound.

Also according to the present invention there are provided processes for producing the compounds of the present invention and a process for the resolution of the optical isomers of the present invention and salts and esters thereof.

DETAILED DESCRIPTION OF THE INVENTION

The disease diabetes mellitus is characterized by metabolic defects in production and utilization of glucose which result in the failure to maintain appropriate blood sugar levels. The result of these defects is elevated blood glucose or hyperglycemia. Research on the treatment of diabetes has centered on attempts to normalize fasting and postprandial blood glucose levels. Treatments have included parenteral administration of exogenous insulin, oral administration of drugs and dietary therapies.

Two major forms of diabetes mellitus are now recognized. Type I diabetes, or insulin-dependent diabetes, is the result of an absolute deficiency of insulin, the hormone which regulates glucose utilization. Type II diabetes, or insulin-independent diabetes, often occurs in the face of normal, or even elevated levels of insulin and appears to be the result of the inability of tissues to respond appropriately to insulin. Most of the Type II diabetics are also obese.

The compounds of this invention were tested for hypoglycemic and anti-obesity activity according to the following procedure.

Obese mice (C57 Bl/6J (ob/ob)), and/or diabetic mice (C57 Bl/KsJ (db/db)) were obtained from Jackson Laboratories, Bar Harbor, Me. Obese rats (fa/fa) were obtained from Charles River Laboratories, Wilmington, Mass. Obese mice were 8 weeks of age and diabetic mice were 9 weeks of age at the start of the test. Obese rats were 12–14 weeks of age at the start.

The test compounds were dissolved in methanol, mixed with powdered Purina rodent chow on a weight of compound to weight of chow basis and thoroughly dried.

Groups of 6 control mice or rats received vehicle (methanol) treated chow.

Groups of 6 test mice were fed ad libitum for up to seven weeks and food consumption was measured daily by weighing the food bins before and after the addition of fresh chow. Thus, a 40 g mouse, fed the test compound at a concentration of 0.02 percent of the diet, would receive a dose of 20 mg/kg/day if it ate 4 g of chow per day.

Groups of 6 test rats were fed 25 g of chow per day for one month. Except for the first day or two, they consumed all their food each day. When these animals are fed ad libitum, they consume 26 g of chow per day and the compounds have no effect on food consumption.

The mice or rats were weighed before the first treatment and once at the end of each indicated treatment period.

Blood samples were collected before the first treatment and once at the end of each indicated treatment period by retro-orbital puncture using heparinized capillary tubes.

Plasma was separated by centrifugation in a Beckman microfuge for 5 minutes. Plasma glucose concentrations were determined with the Beckman glucose analyzer which uses a glucose oxidase method.

The results of these tests on representative compounds of this present invention and a comparative compound of the prior art appear in Table I-III.

TABLE 1

PLASMA GLUCOSE

| Compound | Type of Mice | Dose (% wt) | Plasma Glucose Levels in mg/100 ml Weeks | | | |
|---|---|---|---|---|---|---|
| | | | 0 | 1 | 4 | |
| (R*,R*)-(−/−)-5(2-((2-(3-chloro-phenyl)-2-hydroxyethyl)amino) propyl)-1,3-benzodioxole-2,2-dicarboxylic acid, dimethyl ester hydrobromide | ob/ob | 0 (control) | 233 | 283 | 275 | |
| | | 0.0005 | 270 | 164 | 179 | |
| | | 0.002 | 276 | 150 | 156 | |
| | | 0.005 | 237 | 143 | 157 | |
| | | | 0 | 1 | 5 | 7 |
| | db/db | 0 (control) | 445 | 496 | 543 | 566 |
| | | 0.0005 | 452 | 162 | 164 | 170 |
| | | 0.002 | 453 | 151 | 150 | 161 |
| | | 0.005 | 447 | 148 | 138 | 180 |
| | | | 0 | 1 | 4 | |
| (R*,R*)-(+/−)-5(2-((2-(3-chloro-phenyl)-2-hydroxyethyl)amino) propyl)-1,3-benzodioxole-2,2-dicarboxylic acid, disodium salt | ob/ob | 0 (control) | 232 | 273 | 245 | |
| | | 0.0005 | 218 | 193 | 240 | |
| | | 0.002 | 220 | 162 | 197 | |
| | | 0.005 | 220 | 145 | 165 | |
| | | | 0 | 1 | 5 | 7 |
| | db/db | 0 (control) | 445 | 496 | 543 | 566 |
| | | 0.002 | 453 | 236 | 190 | 250 |
| | | 0.005 | 452 | 155 | 145 | 165 |
| | | | 0 | 5 | 10 | |
| (R*,S*)-(+/−)-5(2-((2-(3-chloro-phenyl)-2-hydroxyethyl)amino) propyl)-1,3-benzodioxole-2,2-dicarboxylic acid, disodium salt | ob/ob | 0 (control) | 227 | 284 | 213 | |
| | | 0.005 | 218 | 162 | 174 | |
| | | 0.02 | 219 | 135 | 153 | |

TABLE II

CHANGE IN WEIGHT

| Compound | Type of Mice of rat | Dose (% wt) | Change in weight in grams weeks | | | | Average Daily Food Consumption g/animal |
|---|---|---|---|---|---|---|---|
| | | | 1 | 2 | 3 | 4 | |
| (R*,R*)-(+/−)-5(2-((2-(3-chloro-phenyl)-2-hydroxyethyl)amino) propyl)-1,3-benzodioxole-2,2-dicarboxylic acid, dimethyl ester hydrobromide | ob/ob | 0 (control) | 1.4 | 3.7 | 5.4 | 7.2 | 4.5 |
| | | 0.0005 | 0.5 | 2.2 | 3.2 | 5.2 | 5.6 |
| | | 0.002 | −0.3 | 1.1 | 1.6 | 3.2 | 5.6 |
| | | 0.005 | −1.1 | −0.7 | −0.2 | 1.6 | 5.8 |
| | fa/fa | 0 (control) | 18 | 39 | 57 | 72 | 25 |
| | | 0.0006 | 14 | 20 | 27 | 26 | 25 |
| | | 0.002 | 1 | 2 | 3 | 4 | 25 |
| | | 0.006 | 10 | 4 | −15 | −8 | 25 |
| (R*,R*)-(+/−)-5(2-((2-(3-chloro-phenyl)-2-hydroxyethyl)amino) propyl)(-1,3-benzodioxole-2,2-dicarboxylic acid, disodium salt | ob/ob | 0 (control) | 3.1 | 5.6 | 7.0 | 9.3 | 4.5 |
| | | 0.002 | 1.6 | 4.1 | 4.7 | 7.3 | 5.2 |
| | | 0.005 | 0.2 | 1.6 | 2.4 | 4.7 | 5.9 |

TABLE III

PLASMA GLUCOSE COMPARATIVE

| Compound | Type of Mice or rat | Dose (% wt) | Plasma Glucose Level in mg/100 ml Weeks | | |
|---|---|---|---|---|---|
| | | | 0 | 1 | 2 |
| (R*,R*)-(+/−)-(4-(2-((2-(4-chlorophenyl)-2-hydroxyethyl)amino)propyl)phenoxy)-acetic acid, methyl ester** | ob/ob | 0 (control) | 233 | 183 | 252 |
| | | 0.0005 | 232 | 140 | 126 |
| | | 0.0001 | 231 | 143 | 119 |
| | | 0.005 | 231 | 137 | 138 |
| | d/b | 0 (control) | 444 | 349 | 604 |
| | | 0.005 | 440 | 138 | 132 |
| (R*,R*)-(+/−)-alpha-(((2-(1,3-benzodioxol-5-yl)-1-methylethyl)amino)methyl)-3-chlorobenzene-methanol mixture with (R*,S*)-(+/−)alpha-(((2-(1,3-benzodioxol-5-yl)-1-methylethyl)amino)methyl)-3-chlorobenzenemethanol | ob/ob | 0 (control) | 217 | 217 | |
| | | 0.002 | 226 | 234 | |
| | | 0.005 | 227 | 175 | |
| | | 0.02 | 227 | 149 | |
| (R*,S*)-(+/−)-alpha-(((2-(1,3-benzodioxol-5-yl)-1-methylethyl)amino)methyl)-3-chlorobenzene-methanol | ob/ob | 0 (control) | 217 | 217 | |
| | | 0.002 | 228 | 204 | |
| | | 0.005 | 226 | 176 | |
| | | 0.02 | 229 | 128 | |

*prior art compound

The above Table I demonstrates that compounds of the present invention and the pharmaceutically active salts thereof effectively lower blood glucose levels when administered orally to genetic strains of hyperglycemic mice which are animal models of type II diabetes. The compounds of the present invention are also seen, in Table II, to decrease weight gain when administered to genetic strains of mice and rats which are animal models of obesity. The exact mechanism by which they act is not known and the invention should not be construed as limited to any particular mechanism of action.

As effective hypoglycemic and weight loss agents, these compounds are useful for the treatment of hyperglycemia and obesity in Type II diabetes.

SELECTIVITY $\beta$-Adrenergic receptors can be divided into $\beta_1$, $\beta_2$ and $\beta_3$-subtypes. Activation of $\beta_1$-receptors invokes increases in heart rate while activation of $\beta_2$-receptors stimulates glycogen breakdown in muscle and thereby prevents glycogen synthesis. Activation of $\beta_3$-receptors stimulates lipolysis (the breakdown of adipose tissue triglycerides to glycerol and free fatty acids), and thereby promotes the loss of fat mass. Compounds that stimulate $\beta_3$-receptors will have anti-obesity activity. In addition, they have hypoglycemic or anti-diabetic activity, but the mechanism of this effect is unknown. A compound that selectively stimulates $\beta_3$-receptors, i.e., has little or no $\beta_1$ or $\beta_2$-activity, will have the desired anti-diabetic and/or anti-obesity activity, but without the undesirable effects of increased heart rate ($\beta_1$-effect) or muscle tremor ($\beta_2$-effect).

Selectivity of a compound was determined using the following procedures. The effect on heart rate ($\beta_1$-effect) was determined using isolated right atria. Guinea pig hearts were placed in a petri dish containing aerated Krebs Henseleit bicarbonate buffer (KHB) of the following composition (mM): NaCl, 112.9: KCl, 4.7: $KH_2PO_4$, 1.2: $MgSO_4 \cdot 7H_2O$, 1.2: $NaHCO_3$, 25.0: $CaCl_2$, 2.4 and glucose, 11.5. The buffer was continuously aerated with 95% $O_2$- 5% $CO_2$. The right atria were dissected and clamped at one end to a tissue holder and electrode assembly (MRA Corp.) and tied at the other end to a force-displacement transducer (Gould-Statham, Burco). The tissues were maintained at 32° C. in a 50 ml capacity glass chamber (MRA Corp.) preloaded with 0.5 g tension. Heart rate was monitored by a Grass polygragh. After equilibration for two hours, the atria were exposed to $1 \times 10^{-6}$M isoproterenol for 5 minutes. The increase in heart rate was calculated and considered to be the maximum response for that tissue. The tissues were then washed and allowed to equilibrate for 90 minutes. Cumulative concentration-response curves were then determined for each compound or vehicle. All responses were measured 5 minutes post-exposure. The responses of each compound were expressed as a percent of the response to isoproterenol. The molar $EC_{50}$ value is the concentration of compound that gave 50% of its own maximum increase in heart rate.

The $\beta_2$-effect of the compounds was determined by their ability to inhibit the insulin-mediated incorporation of $^{14}C$-glucose into glycogen in isolated muscle. Soleus muscle from mice were dissected, tied at each end, and placed in a clamp to maintain tension. The clamped muscle was added to a vial that contained 2 ml of KHB with 1.5% bovine serum albumin, 0.3 mU/ml insulin, 5 mM (U-$^{14}C$) glucose, and the appropriate additions of compound or vehicle. The vial was gassed with 95% $O_2$-5% $CO_2$, capped, and the tissue incubated for one hour in a rotating water bath at 37° C. The muscle was then removed, rinsed in ice-cold saline, blotted and weighed. It was then added to 1 ml of 30% KOH containing 5 mg/ml of oyster glycogen, boiled for 10 minutes, and 0.4 ml of 2% $Na_2SO_4$ and 3.2 ml of 100% ethanol added. After standing overnight at 4° C., the glycogen was pelleted by centrifugation, washed once with 66% ethanol, and repelleted. The pellet was dissolved in 1 ml of water and the amount of radioactivity present determined by liquid scintillation. The decrease in radioactivity incorporated into glycogen by each compound is expressed as a percentage of the decrease obtained in the presence of $1 \times 10^{-7}$M isoproterenol. The molar $EC_{50}$ value is the concentration of compound that gave 50 percent of its own maximum percentage decrease in insulin-mediated incorporation of $^{14}C$-glucose into glycogen.

The $\beta_3$-effect of the compounds was determined by their ability to stimulate adipocyte lipolysis. Rat epididymal fat pads were excised and placed in 0.9% saline.

Four grams of tissue were transferred to a flask with 20 ml of aerated Krebs-Henseleit bicarbonate (KHB) buffer containing 3% fatty acid-free bovine serum albumin to which 75 mg of crude bacterial collagenase (Worthington) had been added. The tissue was incubated for about 45 minutes at 37° C. with gentle shaking. The cells were then washed three times with two volumes of KHB buffer, filtered through two layers of gauze, and brought to a final volume of 80 ml with KHB buffer. One ml aliquots of the cell suspension were added to plastic test tubes containing the appropriate additions of vehicle or compound. The cells were gassed for 1 minute with 95% $O_2$-5% $CO_2$, capped, and incubated at 37° C. with continuous shaking for a total of 30 minutes. The reaction was stopped by adding 0.1 ml of 30% perchloric acid and 0.1 ml of chloroform. After centrifugation, 0.5 ml of supernatant was transferred to another test tube and neutralized with 0.04 ml of 3M $K_2CO_3$-0.5M triethanolamine. The amount of glycerol generated from the hydrolysis of endogenous triglycerides was determined in a coupled-enzyme spectrophotometric assay. One-tenth milliliter of the neutralized extract was added to a test tube that contained 0.91 ml of an assay mixture comprised of the following: 0.84M glycine, 0.42M hydrazine sulfate, 4.2 mM EDTA, 0.9 mM β-NAD, 9.9 mM $MgCl_2$, 1 mM ATP, 17 U of glycerophosphate dehydrogenase, and 4.3 U of glycerokinase. The test tubes were incubated for 40 minutes at 37° C. with constant shaking. The amount of NADH generated, which is proportional to the amount of glycerol, was determined from the increase in absorbance at 340 nm. This value was corrected for the amount of NADH generated in the absence of glycerol by incubating another aliquot of the neutralized extract with the same assay mixture but without glycerokinase. The molar $EC_{50}$ value is the molar concentration of compound that gave 50% of that compound's own maximum rate of lipolysis.

FIG. 1 shows a comparison of the selectivity of a compound of the present invention CL (R*,R*)-(+/−)-5-(2-((2-(3-chlorophenyl)-2-hydroxyethyl)amino)propyl)-1,3-benzodioxole-2,2-dicarboxylic acid, dimethyl ester hydrobromide with that of the corresponding prior art compound, $BRL_1$ (R*,R*)-(+/−)-(4-(2-((2-(4-chlorophenyl)-2-hydroxyethyl)amino)propyl)phenoxy)-acetic acid, methyl ester (Beecham).

Figure 2:
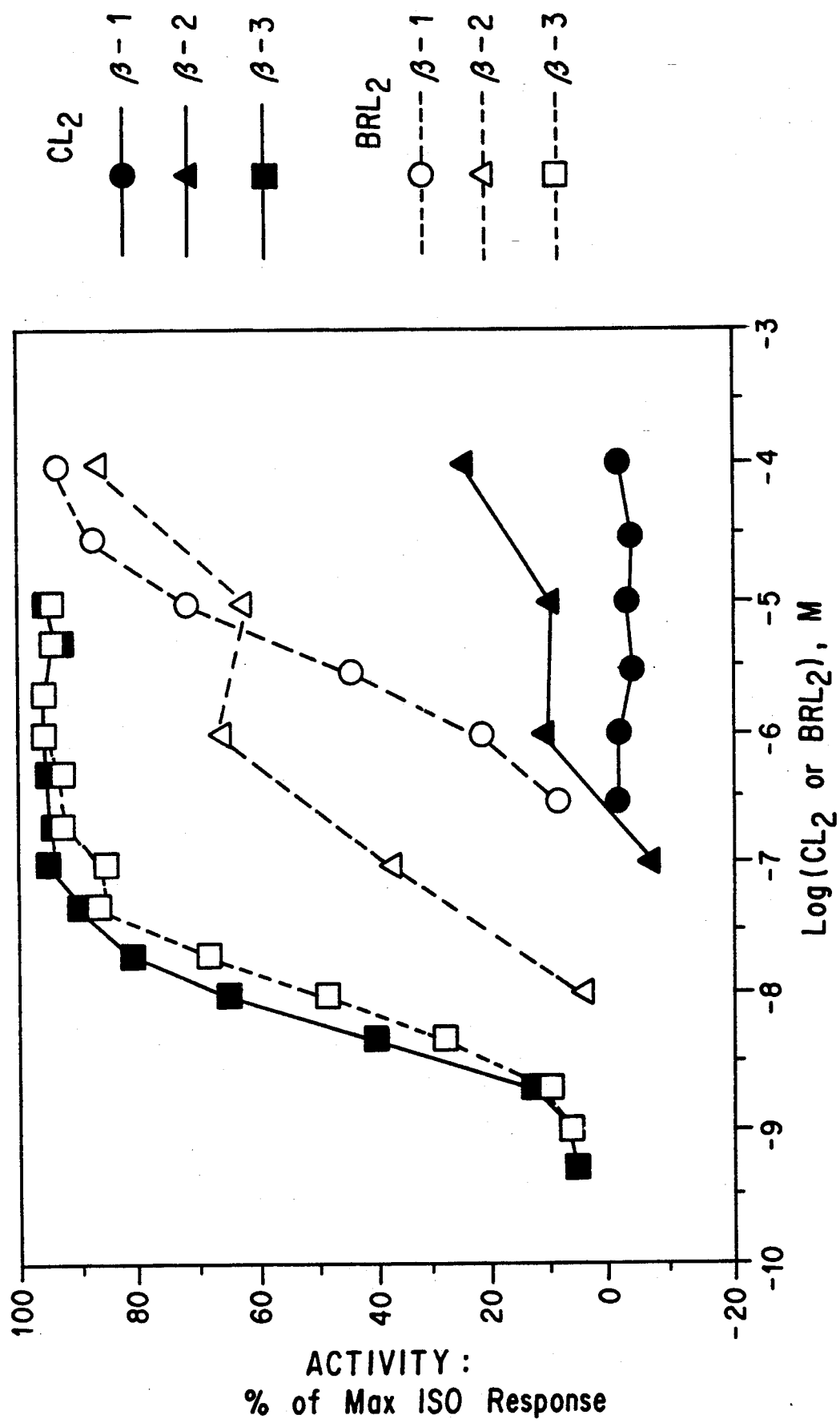
FIG. 2 shows a comparison of the selectivity between a compound of the present invention and a prior art compound

The results indicate that prior art compound $BRL_1$ has slightly greater $\beta_3$ potency, but that it also has more of the undesirable $\beta_1$ and $\beta_2$ activities than does $CL_1$. FIG. 2 shows a comparison of the selectivity of a compound of the present invention $CL_2$ (R*,R*)-(+/−)-5(2-((2-(3-chlorophenyl)-2-hydroxyethyl)amino)-propyl)-1,3-benzodioxole-2,2-dicarboxylic acid, disodium salt with the corresponding prior art compound, BRL2 (R*,R*)-(+/−)-alpha-(((2-(1,3-benzodioxol-5-yl)-1-methylethyl)amino) methyl)-3-chlorobenzenemethanol (Beecham).

The results indicate that $CL_2$ has slightly greater $\beta_3$ potency than does $BRL_2$. $CL_2$ has no measurable $\beta_1$ activity whereas $BRL_2$ has significant $\beta_1$ activity. $CL_2$ showed only minimal $\beta_2$ activity at $1 \times 10^{-4}$M whereas $BRL_2$ was a full agonist with measurable activity at $1 \times 10^{-7}$M. Thus, both of the prior art compounds have more of the undesirable activities than do the corresponding compounds of the present invention. These results are summarized in Table IV below.

Table IV also summarizes the relative $\beta_3$ potencies of the resolved forms (RR and SS) of both the salt ($CL_2$) and methyl ester ($CL_1$). It can be seen from this data that the majority of activity resides with the RR isomer in each case. In the case of the disodium salts, the RR enantiomer is 47 fold more potent than the SS enantiomer. In the case of the methyl ester, the RR isomer is 36 fold more potent.

TABLE IV $\beta_3$ - SELECTIVITY COMPARISON

| Compound | Lipolysis ($\beta_3$) ($EC_{50}$, M) | R.A. Rate ($\beta_1$) ($EC_{50}$, M) | Glycogen Synthesis ($\beta_2$) ($EC_{50}$, M) |
|---|---|---|---|
| Salts: | | | |
| $CL_2$ | $6 \times 10^{-9}$ | $>10^{-3}$ | $>1 \times 10^{-4}$ |
| $CL_3$ | $3 \times 10^{-9}$ | — | — |
| $CL_4$ | $1.4 \times 10^{-7}$ | — | — |
| $BRL_2$** | $9 \times 10^{-9}$ | $5.6 \times 10^{-6}$ | $8 \times 10^{-7}$ |
| Esters: | | | |
| $CL_1$ | $3 \times 10^{-8}$ | $1.4 \times 10^{-8}$ | $8 \times 10^{-7}$ |
| $CL_5$ | $8 \times 10^{-9}$ | — | — |
| $CL_6$ | $2.9 \times 10^{-7}$ | — | — |
| $BRL_1$** | $1.3 \times 10^{-8}$ | $2 \times 10^{-7}$ | $1.2 \times 10^{-7}$ |
| Isoproterenol | $1.2 \times 10^{-8}$ | $1.5 \times 10^{-9}$ | $8 \times 10^{-9}$ |

$\beta_3$ - SELECTIVITY (($EC_{50}$ - $\beta_1$ or $\beta_2$)/($EC_{50}$ - $\beta_3$))

| | Selectivity for Lipolysis over: | | Relative Selectivity (CL/BRL) | |
|---|---|---|---|---|
| | Atria | Gly. Syn. | Atria | Gly. Syn. |
| Salts: | | | | |
| $CL_2$ | >167,000 | >16,700 | >268 | >188 |
| $BRL_2$** | 622 | 89 | | |
| Esters: | | | | |
| $CL_1$ | 47 | 27 | 3.1 | 3.0 |
| $BRL_1$** | 15 | 9 | | |
| Isoproterenol | 0.1 | 0.7 | | |

$CL_1$ = (R*,R*)-(+/−)-5-(2-((2-(3-chlorophenyl)-2-hydroxyethyl amino)propyl)-1,3-benzodioxole-2,2-dicarboxylic acid, dimethyl ester hydrobromide
$CL_2$ = (R*,R*)-(+/−)-5-(2-((2-(3-chlorophenyl)-2-hydroxyethyl amino)propyl)-1,3-benzodioxole-2,2-dicarboxylic acid, disodium salt
$BRL_1$ = (R*,R*)-(+/−)-(4-(2-((2-(4-chlorophenyl)-2-hydroxyethyl)amino)propyl)phenoxy)-acetic acid, emthyl ester
$BRL_2$ = (R*,R*)-(+/−)-(4-(2-((2-(3-chlorophenyl)-2-hydroxyethyl)amino)propyl)phenoxy)-acetic acid, monosodium salt
**comparative example
$CL_3$ = (R,R)-(+/−)-5-(2-((2-(3-chlorophenyl)-2-hydroxyethyl)-amino)propyl)-1,3-benzodioxole-2,2-dicarboxylic acid, disodium salt.
$CL_4$ = (S,S)-(+/−)-5-(2(2-(3-chlorophenyl)-2-hydroxyethyl)-amino)propyl)-1,3-benzodioxole-2,2-dicarboxylic acid, disodium salt.
$CL_5$ = (R,R)-(+/−)-5-(2-((2-(3-chlorophenyl)-2-hydroxyethyl)-amino)propyl)-1,3-benzodioxole-2,2-dicarboxylic acid, dimethyl ester hydrobromide.
$CL_6$ = (S,S)-(+/−)-5-(2-((2-(3-chlorophenyl)-2-hydroxyethyl)-amino)propyl)-1,3-benzodioxole-2,2-dicarboxylic acid, dimethyl ester hydrobromide.

The results indicate that the compounds of the present invention, $CL_2$ and $CL_1$ are 200 and 3 times more selective for lipolysis than are the prior art compounds, $BRL_2$ and $BRL_1$ respectively.

In addition to the abilities of the compounds of the present invention described hereinabove, some of the compounds of the present invention are useful in the preparation of other compounds of the present invention.

The compounds of the present invention may generally be prepared according to the following process, the process comprising:

(a) reacting a compound of the formula

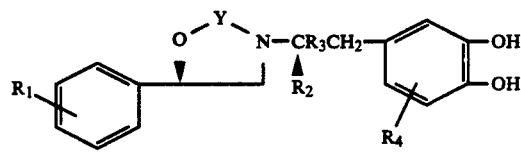

with a ketalizing reagent of the formula

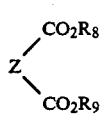

wherein $R_1$, $R_2$, $R_3$ and $R_4$ are as above-defined in relation to formula (XIV) and $R_8$ and $R_9$ are $C_1$ to $C_4$ alkyl and Z is dihalomethylene, carbonyl or thiocarbonyl to produce a compound of the formula

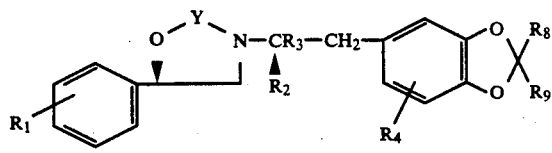

wherein $R_1$, $R_2$, $R_3$, $R_4$ and $R_8$ and $R_9$ are as above defined; and, either (b)(i) reacting the product of step (a) with a base followed by an acid and alcohol to produce a compound of the formula

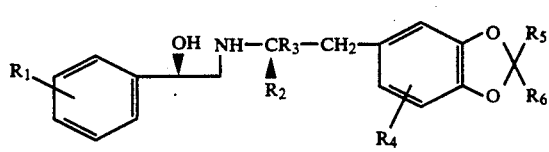

wherein $R_1$, $R_2$, $R_3$ and $R_4$ are as defined above and $R_5$ and $R_6$ are alkoxycarbonyl; and optionally (b)(ii) reacting the product of step (b)(i) with a reagent or reagents for converting the groups represented by $R_5$ and $R_6$ to carboxy, hydroxymethyl, —CH$_2$OCH$_2$COOR$_7$ and CH$_2$OCH$_2$OR$_7$ wherein $R_7$ is hydrogen or $C_1$ to $C_4$ alkyl; or (c)(i) reacting the product of step (a) with a carbonyl reducing agent to form a compound of the formula

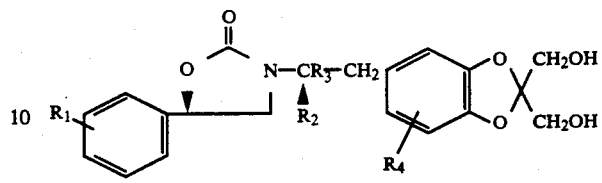

wherein $R_1$, $R_2$, $R_3$ and $R_4$ are as defined above; and (c)(ii) reacting the product of (c)(i) with a reagent or reagents for converting the CH$_2$OH groups to a —CH$_2$OCH$_2$COOR$_7$ group or a —CH$_2$OCH$_2$CH$_2$OR$_7$ group wherein $R_7$ is as defined above; or (c)(iii) reacting the product of step (c)(ii) with a base to produce a compound of the formula

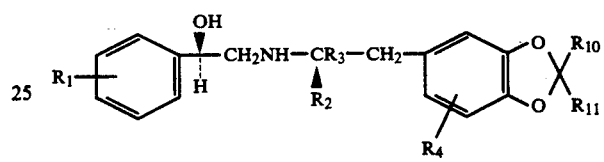

wherein $R_{10}$ and $R_{11}$ are selected from a —CH$_2$OCH$_2$COOR$_7$ group, a —CH$_2$OCH$_2$CH$_2$OR$_7$, group and $R_7$ is as above defined.

Any conventional ketalizing reagents, bases, acids alcohols, reagents for converting to defined groups and carbonyl reducing agents known to those skilled in the art may be employed and are contemplated by the present invention.

In preferred embodiments of the present invention, the following reaction scheme may be employed.

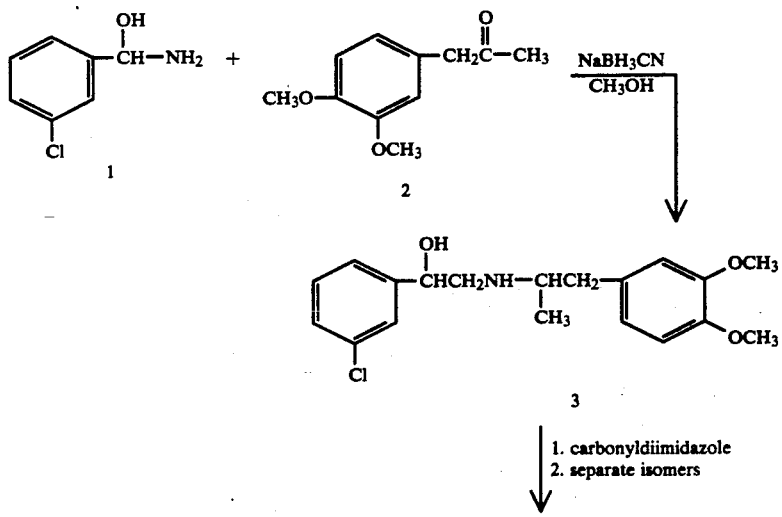

-continued
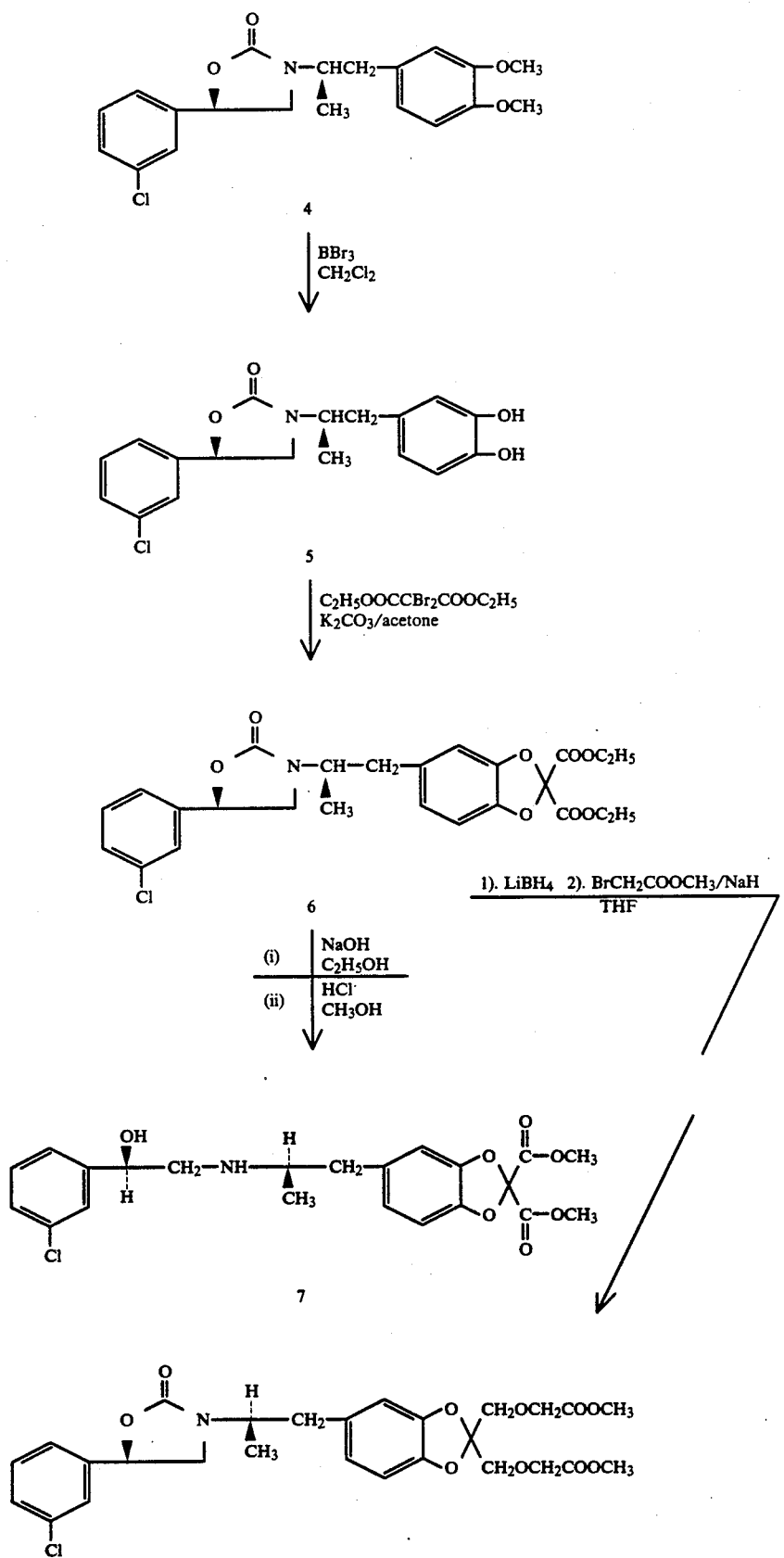

-continued

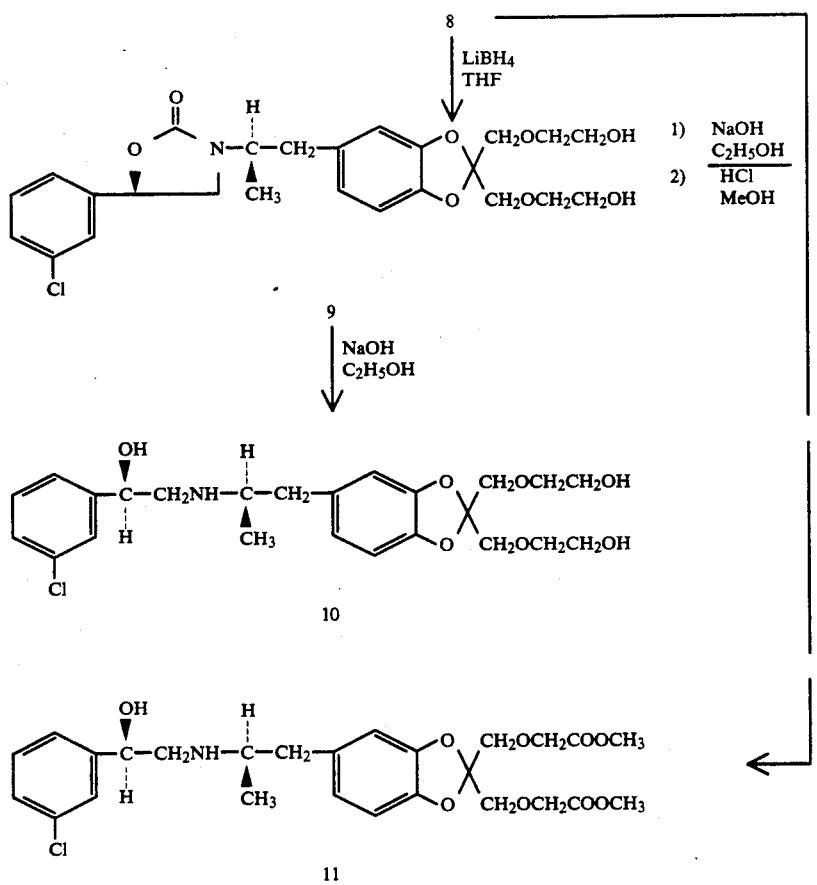

In accordance with the above preferred reaction scheme 2-(3-chlorophenyl)-2-hydroxyethylamine 1, and 3,4-dimethoxyphenylacetone 2 are reacted with sodium cyanoborohydride in methanol, giving 3-chloroalpha-(((2-(3,4-dimethoxyphenyl)-1-methylethyl)amino)-methyl) benzenemethanol 3 which is reacted with carbonyl diimidazole and triethylamine in tetrahydrofuran, followed by separation of isomers, giving cyclized derivative 4 which is reacted with boron tribromide in dichloromethane, giving (R*,R*)-(+/−)-5-(3-chlorophenyl)-3-(2-(3,4-dihydroxy phenyl)-1-methylethyl)2-oxazolidinone 5. Compound 5 is then reacted with diethyl dibromomalonate and anhydrous potassium carbonate in acetone, giving (R*,R*)-(+/−)-5-(2-(5-(3-chlorophenyl)-2-oxo-3-oxazolidinyl)propyl)-1, 3-benzodioxole-2,2-dicarboxylic acid, diethyl ester 6 which is then reacted first with sodium hydroxide in ethanol and then with hydrogen chloride gas in methanol, giving the product (R*,R*)-(+/−) 5-(2-((2-(3-chlorophenyl) 2-hydroxyethyl)-amino)propyl)-1,3-benzodioxole-2, 2-dicarboxylic acid, dimethyl ester 7.

Compound 6 may alternatively be reacted with lithium borohydride in anhydrous tetrahydrofuran followed by reaction with sodium hydride and methyl bromoacetate in anhydrous tetrahydrofuran, giving (R*,R*)-(+/−)-((5-(2((5-(3-chlorophenyl)-2-oxo)-3-oxazolidinyl)propyl)-1,3-benzodioxole-2,2diyl)bis(-methyleneoxy)) bis acetic acid, dimethyl ester 8 which is then reacted with lithium borohydride in anhydrous tetrahydrofuran, giving (R*,R*)-(+/−)-3-(2-((2,2-bis((2-hydroxyethoxy) methyl)-1,3-benzodioxole-5-yl)-1-methylethyl)-5-(3-chlorophenyl)2-oxazolidinone 9. Compound 9 is then refluxed with sodium hydroxide in ethanol, under argon, giving (R*,R*)-(+/−)-alpha-(((2-(2,2-bis((2-hydroxyethoxy)-methyl)-1,3-benzodioxole-5-yl)-1-methylethyl)amino)-methyl)-3-chlorobenzenemethanol 10.

Alternatively compound 8 may be refluxed with sodium hydroxide in ethanol, then neutralized and reacted with hydrogen chloride gas in methanol to derive the product 11.

In another preferred embodiment, optical isomers of the present invention and the derivatives, salts and esters thereof may be resolved by a process comprising: (a) attaching a chiral auxiliary group at the N-9 position of a mixture of (+) and (−) enantiomers of the compounds to form a new pair of diastereoisomers; (b) separating the new pair of diastereoisomers and recovering the new (+) or (−) enantiomer; and (c) converting the substantially pure new diastereoisomer into the corresponding desired substantially pure (+) or (−) enantiomer of a derivative, salt or ester of the compound.

In a preferred embodiment, the following Scheme II may be employed.

SCHEME II

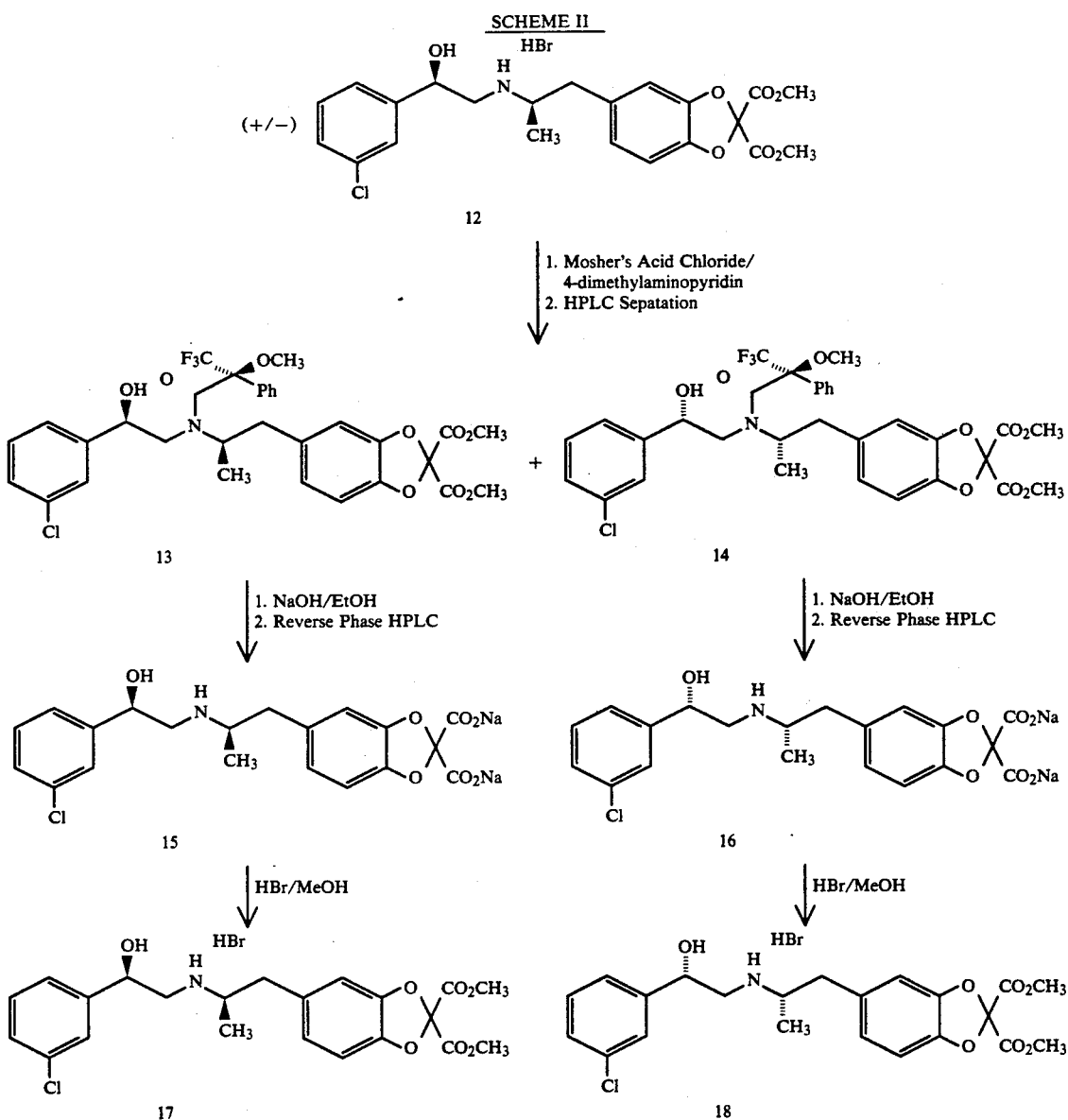

In accordance with the reaction sequence outlined in Scheme II, 1,3-benzodioxole-2,2-dicarboxylic acid, 5-(2-((2-(3-chlorophenyl)-2-hydroxyethyl)amino) propyl-, dimethyl ester, hydrobromide (R*, R*)-(+/−)-, (12) is treated with the acid chloride derived from (S)-(−)--methoxy- -trifluoromethylphenylacetic acid (Mosher's acid). The diastereomeric amides 13 and 14 are separated by preparative HPLC, treated with sodium hydroxide, and the disodium salts 15 and 16 (pure enantiomers), respectively are isolated by reverse phase column chromatography. Treatment of each salt with hydrobromic acid in methanol yields each diester, 1,3-benzodioxole-2,2-dicarboxylic acid, 5-(2-((-(3-chlorophenyl)-2-hydroxyethyl)amino)propyl-, dimethyl ester, hydrobromide (R,R) (17) and 1,3-benzodioxole-2,2-dicarboxylic acid, 5-(2-((2-(3-chlorophenyl)-2-hydroxyethyl)amino)propyl-, dimethyl ester hydrobromide (S,S) (18) respectively. In a similar manner, the corresponding diethyl and diisopropyl esters can be prepared.

Repeating the above sequence starting with 1,3-benzodioxole-2,2-dicarboxylic acid, 5-((2-(3-chlorophenyl)-2-hydroxyethyl)amino)propyl-, dimethyl ester, hydrobromide (R*,S*)-(+/-) yields both enantiomers 1,3-benzodioxole-2,2-dicarboxylic acid, 5-(2-((2-(3-chlorophenyl)-2-hydroxyethyl)amino)propyl-, dimethyl ester, hydrobromide (R,S) and 1,3-benzodioxole-2,2-carboxylic acid, 5-(2-((2-(3-chlorophenyl)-2-hydroxyethyl)amino)propyl-, dimethyl ester, hydrobromide (S,R) respectively. In a similar manner, the corresponding diethyl and diisopropyl esters can be prepared.

Alternatively, the chiral synthesis of the compounds of the present invention may generally be prepared according to the following process, the process comprising;

(a)(i) reacting an optically active compound of the formula

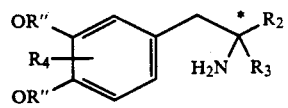

wherein $R_2$, $R_3$ and $R_4$ are as above defined in relation to formula (XIV) and $R''$ is $C_1$ to $C_4$ alkyl with a compound of the formula

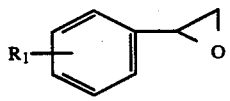

wherein $R_1$ is as above defined in relation to formula (XIV) to produce a compound of the formula

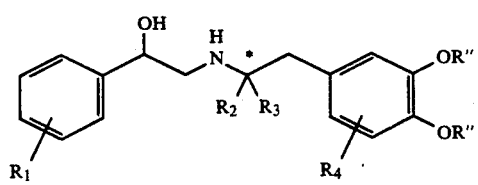

wherein $R_1$, $R_2$, $R_3$, $R_4$, and $R''$ are as defined above;

(b)(i) reacting the product of step (a)(i) with a cyclizing reagent followed by separating the diastereoisomers and recovering the new (+) or (−) enantiomer; or (a)(ii) reacting an optically active compound of the formula

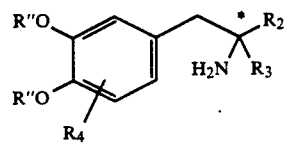

wherein $R_2$, $R_3$, $R_4$ and $R''$ are as above defined with an optically active compound of the formula

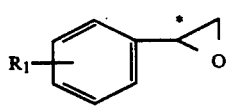

wherein $R_1$ is as above defined to produce a compound of the formula

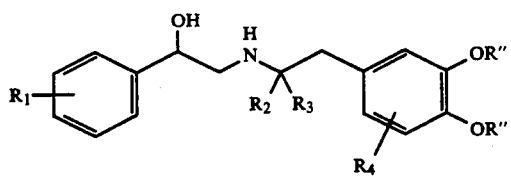

wherein $R_1$, $R_2$, $R_3$, $R_4$ and $R''$ are as defined above and (b)(ii) optionally, reacting said compound with a cyclizing reagent to produce a compound of the formula

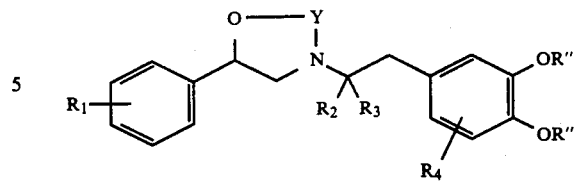

wherein $R_1$, $R_2$, $R_3$, $R_4$, Y and $R''$ are as defined above, and (c) recovering the substantially pure new enantiomers of steps (b)(i), (a)(ii) or (b)(ii) and if desired converting said substantially pure (+) or (−) enantiomer into the corresponding derivative, salt or ester of the compounds of the present invention.

Further, the present invention provides a process for producing the initial reactant of the above process, having the general formula

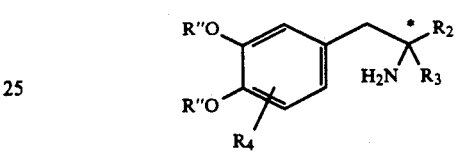

wherein $R_2$ and $R_3$ may be the same or different and are selected from the group consisting of hydrogen and $C_1$-$C_4$ alkyl and $R''$ are independently selected from $C_1$ to $C_4$ alkyl and $R^4$ is selected from the group consisting of hydrogen, $C_1$-$C_4$ alkyl, $C_1$-$C_4$ alkoxy, hydroxy, halogen, trifluoromethyl, carboxy, hydroxyalkyl, alkoxycarbonyl, $C_1$ to $C_4$ thioalkyl, sulfonyl and sulfinyl; the process comprising (a) reacting a compound of the formula

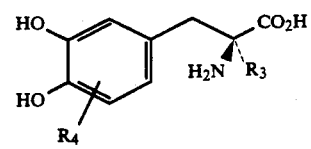

with a carboxylating reagent to produce a compound of the formula

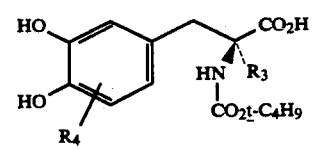

wherein $R_3$ and $R_4$ are as above defined, and (b) reacting the product of step (a) with an alkylating agent to produce a compound of the formula

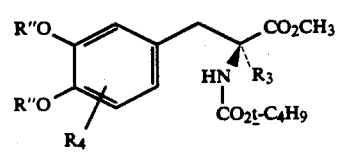

wherein $R_3$, $R_4$, and $R''$ are as above defined, and (c) reacting the product of step (b) with a selective reducing agent to produce a compound of the formula

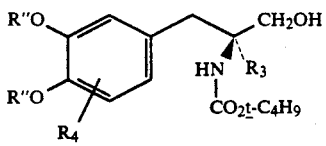

wherein $R_3$, $R_4$, and $R''$ are as above defined, and (d) reacting the product of step (c) with a sulfonylating agent to produce a compound of the formula

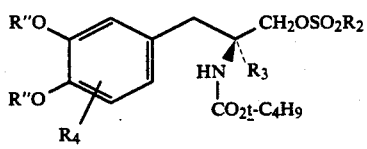

wherein $R_2$, $R_3$, $R_4$, and $R''$ are as above defined, and (e) reacting the product of step (d) with an acid followed by hydrogen and palladium to produce said compound.

More specifically, the chiral synthesis may be carried out by performing the synthetic reaction sequence outlined in Scheme III. L-DOPA 19 is treated with di-t-butyl-dicarbonate in dimethylformamide, giving (S)-N-(1-(1,1-dimethylethoxy)carbonyl)-3-hydroxy-L-tyrosine 20 which is reacted with methyl iodide and anhydrous potassium carbonate in acetone, giving (S)-N-(1,1-dimethylethoxy)carbonyl)-3,4-dimethoxy-L-phenylalanine methyl ester 21 which is reduced with lithium borohydride giving (S)-1,1-dimethylethyl-(2-(3,4-dimethoxyphenyl)-1-(hydroxymethyl)ethyl) carbonate 22, which is reacted with methanesulfonyl chloride and triethylamine in methylene chloride, giving (S)-1,1-dimethylethyl-(2-(3,4-dimethoxyphenyl)-1(((methylsulfonyl) oxy)methyl)ethyl)carbamate 23. Compound 23 is treated with trifluoroacetic acid and then is reduced using 10% Pd/C and hydrogen giving (R)-3,4-dimethoxy- -methylbenzeneethanamine 24. The compound 24 is treated with 3-chlorostyrene oxide 25 and N-(trimethylsilyl) acetamide giving a mixture of (R,S)- and (S,S)-3-chloro-(((2-(3,4-dimethoxyphenyl)-1-methylethyl)amino)methyl) benzenemethanol 26. Reaction of 26 with carbonyl diimidazole and triethylamine in tetrahydrofuran, followed by chromatographic separation of the diastereomers gives cyclized derivative 27, which is reacted with boron tribromide in dichloromethane, giving (R,R)-5-(3-chlorophenyl)-3-(2-(3,4-dihydroxyphenyl)-1-methylethyl)-2-oxazolidinone 28. Compound 28 is then reacted with diethyl dibromomalonate and anhydrous potassium carbonate in acetone, giving (R,R)-5-(2-(5-(3-chlorophenyl)-2-oxo-3-oxazolidinyl)propyl)-1,3-benzodioxole-2,2-dicarboxylic acid, diethyl ester 29. Compound 29 is reacted with 5N sodium hydroxide in ethanol and then isolated by reverse phase chromatography to give (R,R)-1,3-benzodioxole-2,2-dicarboxylic acid, 5-(2-((2-(3-chlorophenyl)-2-hydroxyethyl)amino)propyl)-, disodium salt 15.

Alternatively, reacting compound 24 with (R)-3-chlorostyrene oxide, enantiomerically pure 15 is prepared. Enantiomerically pure epoxides can be prepared by asymmetric reduction of the corresponding x-chloroketone as described by Corey, J. Am. Chem, Soc., 109, 5551 (1987), followed by base catalyzed closure to the epoxide.

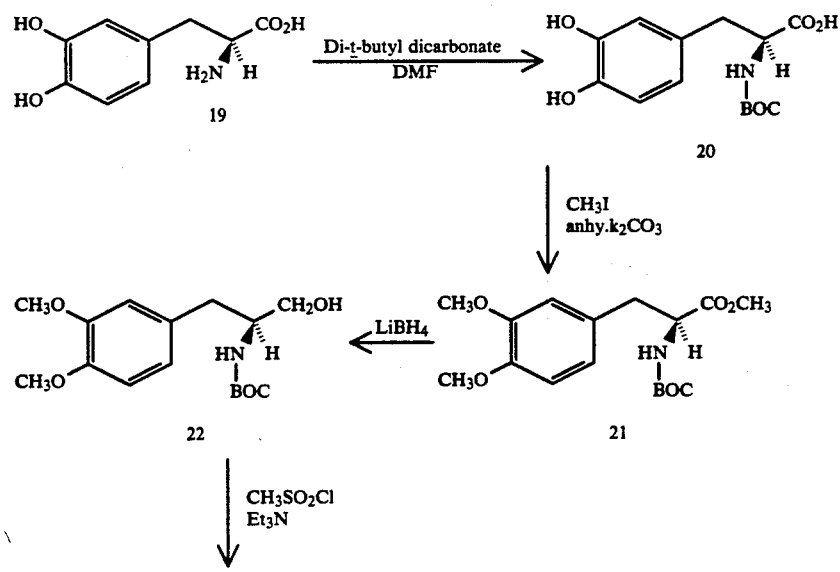

-continued
SCHEME III
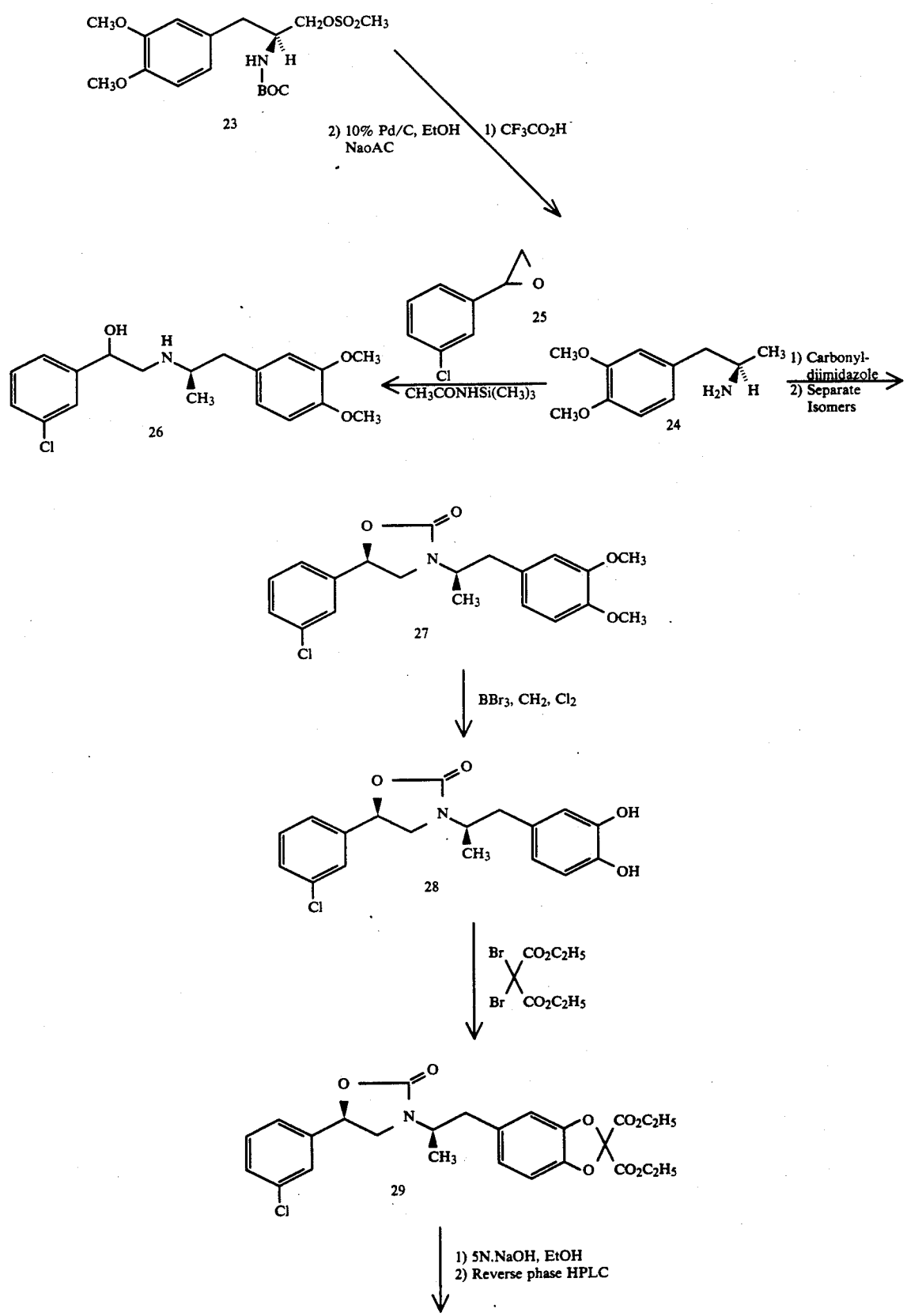

-continued
SCHEME III

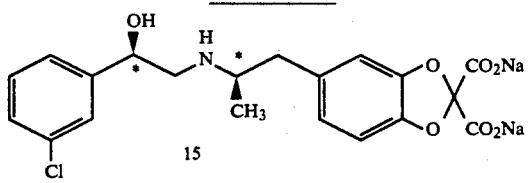

15

The active compounds of the present invention may be orally administered as a pharmaceutical composition, for example, with an inert diluent, or with an assimilable edible carrier, or they may be enclosed in hard or soft shell capsules, or they may be compressed into tablets, or they may be incorporated directly with the food of the diet. For oral therapeutic administration, these active compounds may be incorporated with excipients and used in the form of tablets, pills, capsules, ampules, sachets, elixirs, suspensions, syrups, and the like. Such compositions and preparations should contain at least 0.1 percent of active compound The percentage of active compound in these compositions may, of course, be varied and may conveniently be between about 2 percent to about 60 percent of the weight of the unit. The amount of active compound in such therapeutically useful compositions is such that an effective dosage will be obtained.

The effective dosage of active ingredient employed may vary depending on the particular compound employed, the mode of administration, the condition being treated and the severity of the condition being treated.

When treating diabetes mellitus and/or hyperglycemia generally satisfactory results are obtained when the compounds of the present invention are administered at a daily dosage of from about 0.1 milligram to about 1 milligram per kilogram of animal body weight, preferably given in divided doses two to six times a day, or in sustained release form. For most large mammals, the total daily dosage is from about 3.5 milligrams to about 140 milligrams, preferably from about 3.5 milligrams to about 5 milligrams. In the case of a 70 kg adult human, the total daily dose will generally be from about 7 milligrams to about 70 milligrams. This dosage regimen may be adjusted to provide the optimal therapeutic response.

When treating obesity, in conjunction with diabetes and/or hyperglycemia, or alone, generally satisfactory results are obtained when the compounds of the present invention are administered at a daily dosage of from 1 milligram to about 10 milligrams per kilogram of animal body weight, preferably given in divided doses two to six times a day, or in sustained release form. For most large mammals, the total daily dosage is from about 35 milligrams to about 1,400 milligrams, preferably from about 35 milligrams to about 50 milligrams. In the case of a 70 kg adult human, the total daily dose will generally be from about 70 milligrams to about 700 milligrams. This dosage regimen may be adjusted to provide the optimal therapeutic response.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

These active compounds may also be administered parenterally. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

The compounds of the present invention also possess utility for increasing lean meat deposition and/or improving lean meat to fat ratio in edible animals, i.e. ungulate animals and poultry.

Animal feed compositions effective for increasing lean meat deposition and for improving lean meat to fat ratio in poultry, swine, sheep, goats, domestic pets and cattle are generally prepared by mixing the compounds of the present invention with a sufficient amount of animal feed to provide from about 1 to 1000 ppm of the compound in the feed.

Animal feed supplements can be prepared by admixing about 75% to 95% by weight of a compound of the present invention with about 5% to about 25% by weight of a suitable carrier or diluent. Carriers suitable for use to make up the feed supplement compositions include the following: alfalfa meal, soybean meal, cottonseed oil meal, linseed oil meal, sodium chloride, cornmeal, cane molasses, urea, bone meal, corncob meal and the like. The carrier promotes a uniform distribution of the active ingredients in the finished feed into which the supplement is blended. It thus performs an important function by ensuring proper distribution of the active ingredient throughout the feed.

If the supplement is used as a top dressing for the feed, it likewise helps to ensure uniformity of distribution of the active material across the top of the dressed feed.

The prefered medicated swine, cattle, sheep and goat feed generally contain from 0.01 to 400 grams of active ingredient per ton of feed, the optimum amount for these animals usually being about 50 to 300 grams per ton of feed.

The preferred poultry and domestic pet feeds usually contain about 0.01 to 400 grams and preferably 10 to 400 grams of active ingredient per ton of feed.

For parenteral administration the compounds of the present invention may be prepared in the form of a paste or a pellet and administered as an implant, usually under the skin of the head or ear of the animal in which increase in lean meat deposition and improvement in lean mean to fat ratio is sought In general, parenteral administration involves injection of a sufficient amount of the compounds of the present invention to provide the animal with 0.001 to 100 mg/kg/day of body weight of the active ingredient. The preferred dosage for swine, cattle, sheep and goats is in the range of from 0.001 to 50 mg/kg/day of body weight of active ingredient; whereas, the preferred dose level for poultry and domestic pets is usually in the range of from 0.001 to 35 mg/kg/day of body weight.

Paste formulations can be prepared by dispersing the active compound in a pharmaceutically acceptable oil such as peanut oil, sesame oil, corn oil or the like.

Pellets containing an effective amount of the compounds of the present invention can be prepared by admixing the compounds of the present invention with a diluent such as carbowax, carnuba wax, and the like, and a lubricant, such as magnesium or calcium stearate, can be added to improve the pelleting process.

It is, or course, recognized that more than one pellet may be administered to an animal to achieve the desired dose level which will provide the increase in lean meat deposition and improvement in lean meat to fat ratio desired. Moreover, it has been found that implants may also be made periodically during the animal treatment period in order to maintain the proper drug level in the animal's body.

The method of the present invention has several advantages; for the pet owner or veterinarian who wishes to increase leaness and trim unwanted fat from pet animals, the present invention provides the means by which this can be accomplished. For the poultry men and swine raisers, using the method of the present invnetion yields leaner animals which command higher prices from the meat industry.

The results of animal growth regulant evaluation of compounds of the invention appear in Table V.

Antilipogenic Evaluation of Test Compounds—Mouse Study

CFI female mice, 55 days old, are weighed in groups of 5 and allotted to cages to minimize weight variation among cages. Treatments are randomly assigned to cages.

Each of the treatments are tested in 1 to 3 replicates, i.e., in 3 cages of 5 mice each. There are 10 cages of 5 control mice each. Test compounds are mixed in the diet at the dosage level indicated. Feed and Water are offered ad libitum for a 12-day test period. The mice are weighed as a group of 5 and the weight gain determined. The mice are sacrificed by cervical dislocation. The right uterine fat pad of each mouse is removed. The fat pads for each cage of 5 mice are weighed as a unit. The fat versus body weight ratio is determined using the absolute weights of the fat pads and the absolute body weight.

It can be seen that a reduction in fat pad weights of animals is generally indicative of a reduction of total body fat of the treated animals.

TABLE V

| | REPARTITION EFFECT OF TEST COMPOUNDS | | | |
|---|---|---|---|---|
| COMPOUND | DOSE PPM | % AGR* GAIN OVER CONTROL | % FAT REDUCTION OVER CONTROL | FAT VS BODY WEIGHT RATIO |
| 1,3-Benzodioxole-2,2-dicarboxylic acid, 5-[2-[[2-(3-chlorophenyl)-2-hydroxyethyl]amino]propyl]-, disodium salt, (R*,R*)-(+/−). | 200 | −3.47 | 56.76 | 1:29 |
| 1,3-Benzodioxole-2,2-dicarboxylic acid, 5-[2-[[2-(3-chlorophenyl)-2-hydroxyethyl]amino]propyl]-, dimethyl ester, hydrobromide, (R*,R*)-(+/−). | 200 | 12.90 | 65.51 | 1:43 |
| 1,3-Benzodioxole-2,2-dicarboxylic acid, 5-[2-[[2-(3-chlorophenyl)-2-hydroxyethyl]amino]propyl]-, disodium salt, [R-(R*,R*)]. | 200 | 14.30 | 53.65 | 1:33 |
| | 100 | 4.36 | 58.19 | 1:33 |
| | 50 | −9.23 | 54.35 | 1:26 |
| 1,3-Benzodioxole-2,2-dicarboxylic acid, 5-[2-[[2-(3-chlorohenyl)-2-hydroxyethyl]amino]propyl]-, bis(1-methylethyl)ester, hydrochloride, [R-(R*,R*)]. | 200 | 23.92 | 60.25 | 1:43 |
| | 100 | 9.74 | 60.90 | 1:40 |
| | 50 | 15.58 | 68.01 | 1:32 |
| CONTROL | | | | 1:13 |

*AGR - animal growth regulant gain

The compounds showed good fat reducing activity without interferring with normal animal growth.

DESCRIPTION OF THE PREFERRED EMBODIMENTS

The following specific examples illustrate the present invention. They are not to be construed to limit the claims in any manner whatsoever.

EXAMPLE 1

(R*,R*)-(+/−)-5-(2-((2-(3-Chlorophenyl)-2-hydroxyethyl)amino)propyl)-1,3-benzodioxole-2,2-dicarboxylic acid, dimethyl ester To a mixture of 53.2 g of trimethylsilyl cyanide and 0.5 g of anhydrous aluminum chloride under argon is added dropwise 75.3 g of 3-chlorobenzaldehyde at such a rate that the reaction temperature does not exceed 80° C. The mixture is stirred for 30 minutes, then filtered and washed with ether. The combined filtrate and wash is evaporated to an oil which is distilled on a Kugelrohr giving 107.4 g of O-trimethysilyl-3-chloromandelonitrile (70°-77° C.) as a pale yellow liquid.

To a mixture of 34.7 g of sodium borohydride and 500 ml of tetrahydrofuran is added 104.6 g of trifluoroacetic acid over 40 minutes with stirring in a 20° C. water bath. A 110 g portion of O-trimethyl-silyl-3-chloromandelonitrile is added over 45 minutes, followed by 150 ml of tetrahydrofuran. The mixture is stirred overnight in the 20° C. water bath, then 500 ml of water is added dropwise with ice bath cooling. The mixture is then stirred at room temperature for 1 hour, filtered through diatomaceous earth, washed with tetrahydrofuran and the combined filtrate and wash are concentrated in vacuo until most of the tetrahydrofuran is removed. A 250 ml portion of water and 150 ml of concentrated hydrochloric acid are added, the solution is heated on a steam bath for 1.5 hours, cooled and extracted twice with dichloromethane. The aqueous extracts are combined, made strongly basic with 200 ml of 10N sodium hydroxide in a cooling bath and extracted four times with dichloromethane. The dichloromethane extracts are combined, washed twice with water, dried and evaporated to a yellow oil. This oil is dissolved in ether, filtered through diatomaceous earth and evaporated to an oil. This oil is distilled on a Kugelrohr giving 58.73 g of 2-(3-chlorophenyl)-2-hydroxyethylamine as thick orange oil.

A mixture of 4 g of 2-(3-chlorophenyl)-2-hydroxyethylamine, 4.53 g of 3,4-dimethoxyphenylacetone, 2 g of sodium cyanoborohydride and 40 ml of methanol is stirred for 3 hours and then worked up giving 7.5 g of oil. This oil is purified by chromatography, eluting with hexane:ethyl acetate (1:1), then ethyl acetate, giving 5.35 g of 3-chloro-alpha-(((2-(3,4-dimethoxy phenyl)-1-methylethyl)amino)methyl)benzenemethanol as thick yellow syrup.

A mixture of 4.39 g of 3-chloro-alpha-(((2-(3,4-dimethoxyphenyl)-1-methylethyl)amino)methyl)benzenemethanol, 4.5 g of carbonyldiimidazole, 13 ml of triethylamine and 45 ml of tetrahydrofuran are stirred overnight, then poured into water and extracted twice with ethyl acetate. The extracts are combined, washed twice with 2N hydrochloric acid, once with brine, dried and evaporated to an oil. This oil is chromatographed, eluting with hexane:ethyl acetate (3:1 to 2:1). Fractions 16–19 are combined and evaporated giving 2.02 g of a colorless syrup. To an ice cold solution of 1.71 g of this syrup in 70 ml of dichloromethane is added dropwise 1.3 ml of boron tribromide. The mixture is stirred at 0° to 5° C. for 15 minutes, then at room temperature for 20 minutes, quenched with water and stirred for 20 minutes. The dichloromethane layer is separated, washed with brine, dried and evaporated, giving 1.6 g of (R*,S*)-(+/−)-5-(3-chlorophenyl)-3-(2-(3,4-dihydroxyphenyl)-1-methylethyl)-2-oxazolidinone as a foamy solid.

A mixture of 0.8 g of the above oxazolidinone, 0 74 g of diethyl dibromomalonate, 1.2 g of anhydrous potassium carbonate and 20 ml of acetone are stirred overnight with the addition of a few drops of diethyl dibromomalonate. The mixture is filtered, washed with acetone and the combined filtrate and wash are evaporated to a yellow oil. The oil is purified by flash chromatography, eluting with 5 percent acetone in toluene. The pure fractions are combined and evaporated, giving 766 mg of (R*,S*)-(+/−)-5-(2-(5-(3-chlorophenyl)-2-oxo-3-oxazolidinyl)propyl-1,3-benzodioxole-2,2-dicarboxylic acid, diethyl ester as a colorless oil.

A mixture of 636 mg of the above diethyl ester, 23 ml of 5N sodium hydroxide and 44 ml of ethanol are heated at reflux under argon overnight, then cooled and evaporated. The solid residue is taken up in methanol, placed in an ice bath and hydrogen chloride gas is passed through the solution for 3–4 minutes. This mixture is stirred for 1.5 hours, then poured cautiously into saturated aqueous sodium bicarbonate and extracted with ethyl acetate. This ethyl acetate extract is washed with brine, dried, filtered and evaporated to an oil. This oil is purified by flash chromatography, eluting with ethyl acetate. The pure fractions are combined and evaporated, giving 264 mg of the desired product as a colorless oil.

EXAMPLE 2

(R*,S*)-(+/−)-((5-(2-(5-(3-chlorophenyl)-2-oxo-3-oxazolidinyl)propyl-1,3-benzodioxole-2,2-diylbis(methyleneoxy)bis acetic acid, dimethyl ester A mixture of 1.63 g of (R*,S*)-(+/−)-5-(2-(5 (3-chlorophenyl)-2-oxo-3-oxazolidinyl)propyl-1,3-benzodioxole-2,2-dicarboxylic acid, diethyl ester and 2.5 g of lithium borohydride in 25 ml of anhydrous tetrahydrofuran are reacted, giving 1.26 g of the corresponding alcohol as a white foam.

A 590 mg portion of 60 percent sodium hydride is washed three times with hexane. To this is added under argon, 10 ml of dry tetrahydrofuran and, over 5 minutes, a solution of 1.24 g of (R*,R*)-(+/−)-5-(2-(5-(3-chlorophenyl)-2-oxo-3-oxazolidinyl)propyl-1,3-benzodioxole-2,2-dicarboxylic acid in 10 ml of dry tetrahydrofuran. The solution is stirred for 5 minutes, then 1.36 g of methyl bromoacetate is added over 10 minutes. After stirring overnight this mixture is poured into aqueous ammonium chloride and extracted twice with ethyl acetate. The extracts are combined, dried and evaporated to an oil which is purified by chromatography, giving 1.03 g of the desired product as a pale yellow oil.

EXAMPLE 3

(R*,R*)-(+/−)-3-(2-(2,2-Bis((2-hydroxyethoxy)methyl)-1,3-benzodioxol-5-yl)-1-methylethyl)-5-(3-chlorophenyl)-2-oxazolidinone A mixture of 420 mg of (R*,R*)-(+/−)-(5-(2-(5-(3-chlorophenyl)-2-oxo-3-oxazolidinyl)propyl-1,3-benzodioxole)-2,2-diyl)bis(methyleneoxy)bis acetic acid, dimethyl ester, 0.75 g of lithium borohydride and 10 ml of anhydrous tetrahydrofuran are allowed to react for 1.5 hours, giving 340 mg of the desired product as a milky film.

EXAMPLE 4

(R*,R*)-(+/−)-((5-(2-(2-(3-chlorophenyl)-2-hydroxyethyl)amino)propyl)-1,3-benzodioxole-2,2-diyl)bis(methyleneoxy)bis acetic acid, dimethyl ester A mixture of 370 mg of (R*,R*)-(+/−)-(5-(2-(5-(3-chlorophenyl)-2-oxo-3-oxazolidinyl)propyl-1,3-benzodioxole-2,2-diyl)bis(methyleneoxy)bis acetic acid, dimethyl ester, 9 ml of 5N sodium hydroxide and 19 ml of absolute ethanol are refluxed overnight, then cooled, acidified to pH 5 with concentrated hydrochloric acid and evaporated to dryness in vacuo. The residue is dissolved in 20 ml of methanol, then saturated with hydrogen chloride gas and stirred for 1.5 hours. The mixture is poured into aqueous sodium bicarbonate and extracted twice with ethyl acetate. The extracts are combined, washed with brine, dried and evaporated.

The residue is purified by flash chromatography, eluting with ethyl acetate, giving 220 mg of the desired product as a pale yellow thick oil.

EXAMPLE 5

(R*,R*)-(+/−)-alpha-(((2-(2,2-bis((2-hydroxyethoxy)-methyl)-1,3-benzodioxole-5-yl)-1-methylethyl)-amino)-methyl)-3-chlorobenzenemethanol A mixture of 270 mg of (R*,R*)-(+/−)-3-(2-(2,2-bis((2-hydroxyethoxy)methyl)-1,3-benzodioxole-5-yl)-1-methylethyl)-5-chlorophenyl)-2-oxazolidinone, 200 ml of ethanol and 5 ml of 5N sodium hydroxide are refluxed under argon for 8 hours, then poured into salty water and extracted twice with ethyl acetate. The extracts are combined, washed with brine, dried and evaporated. The residue is purified by flash chromatography, eluting with dichloromethane:methanol:ammonium hydroxide (250:35:5). Fractions 3 and 4 are combined and evaporated, giving 170 mg of the desired product as a thick yellow oil.

EXAMPLE 6

1,3-Benzodioxole-2,2-Dicarboxylic Acid, 5-(2-((2-(3-Chlorophenyl)-2-Hydroxyethyl)Amino)Propyl), Disodium Salt, (R*,R*)-(+/−)-

A solution of (1,3-benzodioxole-2,2-dicarboxylic acid, 5-(2-(5-(3-chlorophenyl)-2-oxo-3-oxazolidinyl)-propyl-, diethyl ester, (R*,R*)-(+/−)-, (550 mg 1.09 mmol), 5N NaOH (15 mL) and distilled water (15 mL) is heated at reflux under an argon atmosphere for 17 hours. The solution is cooled, and then acidified to pH 9 using concentrated HCl causing a copious amount of white solid to precipitate. The mixture is filtered and the solid is washed with water. The combined filtrate and water wash (53 mL) is loaded onto a column packed with $C_{18}$ reverse phase silica gel (75 mL) which had first been washed with MeOH (150 mL) and then a pH 8.5 solution and then the product is eluted using MeOH:water (1:1). Evaporation of the product-containing fractions yielded a yellow oil which became a powdery solid upon addition of MeOH. The solid was collected and washed with ether to yield a dry white powder, 395 mg (78%).

EXAMPLE 7

1,3-Benzodioxole-2,2-Dicarboxylic Acid, 5-(2-((2-(3-Chlorophenyl)-2-Hydroxyethyl)Amino)-Propyl)-, Dimethyl Ester, Hydrobromide, (R*,R*)-(+/−)-

Absolute methanol (20 mL) is treated dropwise with distilled acetyl bromide (20 drops) and the solution is stirred for 5 minutes. To this solution is added (R*,R*)-(+/−)-5-(2-((2-(3-chlorophenyl)-2-hydroxyethyl)amino)propyl)-1,3-benzodioxole-2,2-dicarboxylic acid, disodium salt (500 mg, 1.09 mmol) and the solution is stirred for 24 hours at room temperature. The solution is evaporated to give to yield a brown oil which is dissolved in chloroform and filtered to remove sodium bromide. The chloroform is evaporated and ether is added to the resulting brown oil to give a beige solid. The solid is collected and washed with ether to give a dry powder (520 mg, 90%). Recrystallization from acetonitrile-ether yielded the analytical sample, mp 145°-147° C.

EXAMPLE 8 b 1,3-Benzodioxole-2,2-Dicarboxylic Acid, 5-(2-((2-(3-Chlorophenyl)-2-Hydroxyethyl)Amino)-Propyl)-, Disodium salt, (R,R) and 1,3-Benzodioxole-2,2-Dicarboxylic acid, 5-(2-((-(3-Chlorophenyl)-2-Hydroxyethyl)Amino)-Propyl)-, Disodium Salt, (S,S)

A solution of (R*,R*)-(+/−)-5-(2((2-(3-chlorophenyl)-2-hydroxyethyl)amino)propyl)-1,3-benzodioxole-2,2-dicarboxylic acid, dimethyl ester hydrobromide (1.00 g, 1.88 mmol), triethylamine (0.48g, 4.71 mmol) and (S)-(−)-2-trifluoromethyl-2-methoxyphenylacetyl chloride (0.54 g, 2.26 mmol) in 10 mL of methylene chloride is stirred at room temperature for 3 days. The yellow solution is diluted with 50 mL of ether and washed sequentially with 2N HCl, aqueous sodium bicarbonate, and brine. The organic solution is dried ($MgSO_4$), filtered and concentrated to give a yellow oil. Purification by preparative HPLC (silica, hexane: ethyl acetate 4:1) yielded: (1) the less polar isomer, 229 mg (18%) and (2) the more polar isomer, 248 mg (20%), both as dry foams.

The more polar isomer (235 mg, 0.353 mmol) is heated at reflux in a solution of ethanol (4mL) and 5N NaOH (2mL) for 24 hours under argon atmosphere. The solution is cooled and acidified to pH 9 using concentrated HCl causing some white solid to form. The entire mixture is loaded onto a flash chromatography column packed with $C_{18}$ silica (40 mL) which had been prepared as described in the (R*,S*)-5-(2-((2-(3-chlorophenyl)-2-hydroxyethyl)amino)propyl)-1,3-benzodioxole-2,2-dicarboxylic acid, disodium salt experiment. Isolation of the product is accomplished in the same manner as was previously described. The product (single enantiomer), a white powder (117 mg, 71%) is obtained. The other enantiomer is obtained by a similar hydrolysis of the less polar diastereomer.

EXAMPLE 9

(R,R)-1,3-Benzodioxole-2,2-dicarboxylic acid, 5-(2-((2-(3-chlorophenyl)-2 hydroxyethyl)amino)propyl)-, disodium salt A mixture of 25 g of L-DOPA, 27.7 g of di-t-butyl dicarbonate in 300 ml of dimethylformamide is heated at 65° C. for 22 hours, cooled, poured into 5 percent citric acid solution and extracted twice with ethyl acetate. The ethyl acetate extracts are washed with brine, dried, filtered and evaporated to yield 31.0 g of (S)-N-(1,1-dimethylethoxy)carbonyl-3-hydroxy-L-tyrosine, as a brown oil.

A mixture of 31.0 g of the above t-butyl carbonate derivative, 52 ml of iodomethane, and 145 g of anhydrous potassium carbonate in 300 ml of acetone is heated to reflux for 20 hours, cooled, filtered and the solvent evaporated to yield a residue. The residue is then partitioned between water and methylene chloride. The methylene chloride extract is washed with brine, dried, filtered and evaporated to yield 27 g of (S)-N-(1,1-dimethylethoxy)carbonyl-3,4-dimethoxy-L-phenylalanine, methyl ester as a yellow solid.

A mixture of 27.0 g of the above ester derivative, 3.7 g of lithium borohydride and 180 ml of tetrahydrofuran is allowed to react for 18 hours, giving 22.0 g of (S)-1,1-dimethylethyl-(2-(3,4-dimethoxyphenyl)-1-(hydroxymethyl)ethyl)carbamate as a white solid.

To an ice cold solution of 22.0 g of the above hydroxymethyl derivative, 15 ml of triethylamine in 140 ml of anhydrous tetrahydrofuran, is added 7.0 ml of methanesulfonylchloride, stirred at room temperature for 2 hours, diluted with water, and extracted with ethyl acetate. The ethyl acetate extract is washed with 2N hydrochloric acid, 1N sodium hydroxide, brine, and then dried, filtered and evaporated to give 25.0 g of (S)-1, 1-dimethylethyl-(2-(3,4-dimethoxyphenyl)-1-((methylsulfonyl)oxy)methyl)ethyl)carbamate as a white solid.

A mixture of 18.0 g of the above mesyl derivative and 35 ml of trifluoroacetic acid in 80 ml of methyl chloride is reacted for 18 hours and solvent is evaporated to yield a gray oil. The oil is dissolved in ethanol and 15 g of sodium acetate, and 1.8 g of 10 percent palladium on carbon is added. The resulting mixture is then hydrogenated on a Parr shaker overnight. The catalyst is filtered and the filtrate evaporated to yield an oil. The oil is purified by kugelrohr distillation to yield 5.8 g of (R)-3,4-dimethoxymethylbenzeneethanamine as a white solid.

A mixture of 420 mg of the above amine and 311 mg of N-(trimethylsilyl)acetamide in 2 ml of dimethylsulfoxide is stirred at room temperature for 1 hour. A solution of 349 mg of 3-chlorostyreneoxide in 0.3 ml dimethylsulfoxide is added to the above mixture and the resulting mixture is heated at 65° C. to 70° C. for 20 hours, cooled, poured into a mixture of ice and concentrated hydrochloric acid, stirred, basified with 10N NaOH and extracted with ethyl acetate. The ethyl acetate extract is washed with brine, dried, filtered and evaporated to yield an oil which is purified by flash chromatography to yield 489 mg of (R,S) and (S,S)-3-chloro-α-((2-(3,4-dimethoxyphenyl)-1-methylethyl)-amino)methyl)benzenemethanol.

A mixture of 1.4 g of the above benzenemethanol derivatives, 1.39 g of carbonyldiimidazole, 3.5 ml of triethylamine and 15 ml of tetrahydrofuran is stirred overnight, then poured into water and extracted twice with ethyl acetate. The ethyl acetate extract is washed with 2N hydrochloric acid, brine, dried and evaporated to an oil. The oil is chromatographed, eluting with hexane:ethyl acetate (3:1 to 2:1). Fractions containing bottom spot are combined and evaporated giving 318 mg of colorless oil. To an ice cold solution of 300 mg of this oil is added dropwise 0.23 ml of boron tribromide. The mixture is stirred at 0° C. to 5° C. for 15 minutes, then at room temperature for 20 minutes, quenched with water and stirred for 20 minutes. The dichloromethane layer is separated, washed with brine, dried and evaporated giving 254 mg of (R,R)-5-(3-chlorophenyl)-3-(2 (3,4-dihydroxyphenyl)-1-methylethyl)-2-oxazolidinone as a foaming solid.

A mixture of 240 mg of the above oxazolidinone, 234 mg of diethyl bromomalonate, 450 mg of anhydrous potassium carbonate and 10 ml of acetone is stirred overnight, filtered, washed with acetone and evaporated to a brown oil. The oil is purified by flash chromatography, eluting with 5 percent acetone in toluene. The pure fractions are combined and evaporated giving 237 mg of (R,R)-5-(3-chlorophenyl)-2-oxo-3-oxazolidinyl)propyl)-1,3-benzodioxole-2,2-dicarboxylic acid, diethyl ester as a colorless oil.

A mixture of 234 mg of the above diethyl ester, 8.5 ml of 5N sodium hydroxide and 17 ml of ethanol is heated at reflux under argon overnight, cooled and then acidified to pH 9 using concentrated hydrochloric acid causing a copious amount of a white solid to precipitate. The mixture is filtered and the solid is washed with water. The combined filtrate and water wash (22 ml) is loaded onto a column packed with $C_{18}$ reverse phase silica gel, which was first washed with methanol (64 ml), and then a pH 8.5 solution. The product is eluted using methanol:water (1:1). Evaporation of the product containing fractions gives a yellow oil which becomes a powdery solid upon the addition of methanol. The solid is collected and washed with ether to yield 8.5 mg of the compound of this example as a white solid.

EXAMPLE 10

(R*,R*)-(+/−)-5-(2-((2-(3-chlorophenyl)-2-hydroxyethyl)-amino)propyl)-1,3-benzodioxole-2,2-carboxylic acid, diethyl ester, hydrobromide The procedure to prepare the dimethyl ester of Example 7 is repeated, substituting ethanol for methanol to produce the compound of the example as a white powder, mp 174°-176° C.

EXAMPLE 11

(R*,R*)-(+/−)-5-(2-((2-(3-chlorophenyl)-2-hydroxyethyl)-amino)propyl)-1,3-benzodioxole-2,2-dicarboxylic acid, diisopropyl ester, hydrobromide The procedure to prepare the dimethyl ester of Example 7 is repeated, substituting 2-propanol for methanol to produce the compound of the example as an off-white powder, mp 170°-172° C.

EXAMPLES 12-107

The procedure of Example 1 is repeated, except that the substituents on the starting compounds are varied. Table A sets forth the compounds produced in accordance with the present invention.

TABLE A

| EXAMPLE | COMPOUND |
|---|---|
| 12 | 5-(2-((-(2,3-dichlorophenyl)-2-hydroxyethyl) amino)propyl)-1,3-benzodioxole-2,2-dicarboxylic acid, diemthyl ester |
| 13 | 5-(2-((2-(3-chlorophenyl)-2-hydroxyethyl) amino)propyl)-1,3-benzodioxole-2,2-dicarboxylic acid, diethyl ester |
| 14 | 5-(2-((2-(3-chlorophenyl)-2-hydroxyethyl) amino)propyl)-1,3-benzodioxole-2,2-dicarboxylic acid, dibutyl ester |
| 15 | 5-(2-((2-(3-chlorophenyl)-2-hydroxyethyl) amino)butyl)-1,3-benzodioxole-2,2-dicarboxylic acid, dimethyl ester |
| 16 | 5-(2-((-(2-(3,4-dichlorophenyl)-2-hydroxyethyl) amino)butyl)-1,3-benzodioxole-2,2-dicarboxylic acid, diethyl ester |
| 17 | 5-(2-((2-(3-chlorophenyl)-2-hydroxyethyl) amino)butyl)-1,3-benzodioxole-2,2-dicarboxylic acid, dibutyl ester |
| 18 | 5-(2-((2-(3-bromophenyl)-2-hydroxyethyl) amino)propyl)-1,3-benzodioxole-2,2-dicarboxylic acid, dimethyl ester. |
| 19 | 5-(2-((2-(3-bromophenyl)-2-hydroxyethyl) amino)propyl)-1,3-benzodioxole-2,2-dicarboxylic acid, diethyl ester |
| 20 | 5-(2-((2-(3-bromophenyl)-2-hydroxyethyl) amino)propyl)-1,3-benzodioxole-2,2-dicarboxylic acid, dibutyl ester |
| 21 | 5-(2-((2-(3-bromophenyl)-2-hydroxyethyl) amino)butyl)-1,3-benzodioxole-2,2-dicarboxylic acid, dimethyl ester |
| 22 | 5-(2-((2-(3-bromophenyl)-2-hydroxyethyl) amino)butyl)-1,3-benzodioxole-2,2-dicarboxylic acid, diethyl ester |
| 23 | 5-(2-((2-(3-bromophenyl)-2-hydroxyethyl) amino)butyl)-1,3-benzodioxole-2,2-dicarboxylic acid, dibutyl ester |

TABLE A-continued

| EXAMPLE | COMPOUND |
|---|---|
| 24 | 5-(2-((2-(3-fluorophenyl)-2-hydroxyethyl)amino)propyl)-1,3-benzodioxole-2,2-dicarboxylic acid, dimethyl ester |
| 25 | 5-(2-((2-(3-fluorophenyl)-2-hydroxyethyl)amino)propyl)-1,3-benzodioxole-2,2-dicarboxylic acid, diethyl ester |
| 26 | 5-(2-((2-(3-fluorophenyl)-2-hydroxyethyl)amino)propyl)-1,3-benzodioxole-2,2-dicarboxylic acid, dibutyl ester |
| 27 | 5-(2-((2-(3-fluorophenyl)-2-hydroxyethyl)amino)butyl)-1,3-benzodioxole-2,2-dicarboxylic acid, diemthyl ester |
| 28 | 5-(2-((2-(3-fluorophenyl)-2-hydroxyethyl)amino)butyl)-1,3-benzodioxole-2,2-dicarboxylic acid, diethyl ester |
| 29 | 5-(2-((2-(3-fluorophenyl)-2-hydroxyethyl)amino)pentyl)-1,3-benzodioxole-2,2-dicarboxylic acid, dibutyl ester |
| 30 | 5-(2-((2-(3-trifluoromethylphenyl)-2-hydroxyethyl)amino)propyl)-1,3-benzodioxole-2,2-dicarboxylic acid, dimethyl ester |
| 31 | 5-(2-((2-(3-trifluoromethylphenyl)-2-hydroxyethyl)amino)propyl)-1,3-benzodioxole-2,2-dicarboxylic acid, diethyl ester |
| 32 | 5-(2-((2-(3-trifluoromethylphenyl)-2-hydroxyethyl)amino)propyl)-1,3-benzodioxole-2,2-dicarboxylic acid, dibutyl ester |
| 33 | 5-(2-((2-(3-trifluoromethylphenyl)-2-hydroxyethyl)amino)butyl)-1,3-benzodioxole-2,4-dicarboxylic acid, dimethyl ester |
| 34 | 5-(2-((2-(3-trifluoromethylphenyl)-2-hydroxyethyl)amino)butyl)-1,3-benzodioxole-2,2-dicarboxylic acid, diethyl ester |
| 35 | 5-(2-((2-(3-trifluoromethylphenyl)-2-hydroxyethyl)amino)butyl)-1,3-benzodioxole-2,2-dicarboxylic acid, dibutyl ester |
| 36 | 5-(2-((2-(3-methoxyphenyl)-2-hydroxyethyl)amino)propyl)-1,3-benzodioxole-2,2-dicarboxylic acid, dimethyl ester |
| 37 | 5-(2-((2-(3-methoxy-4-chlorophenyl)-2-hydroxyethyl)amino)propyl)-1,3-benzodioxole-2,2-dicarboxylic acid, diethyl ester |
| 38 | 5-(2-((2-(3-methoxyphenyl)-2-hydroxyethyl)amino)propyl)-1,3-benzodioxole-2,2-dicarboxylic acid, dibutyl ester |
| 39 | 5-(2-((2-(3-methoxyphenyl)-2-hydroxyethyl)amino)butyl)-1,3-benzodioxole-2,2-dicarboxylic acid, dimethyl ester |
| 40 | 5-(2-((2-(3-methoxyphenyl)-2-hydroxyethyl)amino)butyl)-1,3-benzodioxole-2,2-dicarboxylic acid, diethyl ester |
| 41 | 5-(2-((2-(3-methoxyphenyl)-2-hydroxyethyl)amino)butyl)-1,3-benzodioxole-2,2-dicarboxylic acid, dibutyl ester |
| 42 | 5-(2-((2-(3-methylphenyl)-2-hydroxyethyl)amino)propyl)-1,3-benzodioxole-2,2-dicarboxylic acid, dimethyl ester |
| 43 | 5-(2-((2-(3-methylphenyl)-2-hydroxyethyl)amino)propyl)-1,3-benzodioxole-2,2-dicarboxylic acid, diethyl ester |
| 44 | 5-(2-((2-(3-methylphenyl)-2-hydroxyethyl)amino)propyl)-1,3-benzodioxole-2,2-dicarboxylic acid, dibutyl ester |
| 45 | 5-(2-((2-(3-methylphenyl)-2-hydroxyethyl)amino)butyl)-1,3-benzodioxole-2,2-dicarboxylic acid, dimethyl ester |
| 46 | 5-(2-((2-(3-methylphenyl)-2-hydroxyethyl)amino)butyl)-1,3-benzodioxole-2,2-dicarboxylic acid, diethyl ester |
| 47 | 5-(2-((2-(3-methylphenyl)-2-hydroxyethyl)amino)butyl)-1,3-benzodioxole-2,2-dicarboxylic acid, dibutyl ester |
| 48 | 5-(2-((2-(3-dimethylaminophenyl)-2-hydroxyethyl)amino)propyl)-1,3-benzodioxole-2,2-dicarboxylic acid, dimethyl ester |
| 49 | 5-(2-((2-(3-dimethylaminophenyl)-2-hydroxyethyl)amino)propyl)-1,3-benzodioxole-2,2-dicarboxylic acid, diethyl ester |
| 50 | 5-(2-((2-(3-dimethylaminophenyl)-2-hydroxyethyl)amino)propyl)-1,3-benzodioxole-2,2-dicarboxylic acid, dibutyl ester |
| 51 | 5-(2-((2-(3-dimethylaminophenyl)-2-hydroxyethyl)amino)butyl)-1,3-benzodioxole-2,2-dicarboxylic acid, diethyl ester |
| 52 | 5-(2-((2-(3-dimethylaminophenyl)-2-hydroxyethyl)amino)butyl)-1,3-benzodioxole-2,2-dicarboxylic acid, dimethyl ester |
| 53 | 5-(2-((2-(3-dimethylaminophenyl)-2-hydroxyethyl)amino)butyl)-1,3-benzodioxole-2,2-dicarboxylic acid, dibutyl ester |
| 54 | 5-(2-((2-(3-carbomethoxyphenyl)-2-hydroxyethyl)amino)propyl)-1,3-benzodioxole-2,2-dicarboxylic acid, dimethyl ester |
| 55 | 5-(2-((2-(3-carbomethoxyphenyl)-2-hydroxyethyl)amino)propyl)-1,3-benzodioxole-2,2-dicarboxylic acid, diethyl ester |
| 56 | 5-(2-((2-(3-carbomethoxyphenyl)-2-hydroxyethyl)amino)propyl)-1,3-benzodioxole-2,2-dicarboxylic acid, dibutyl ester |
| 57 | 5-(2-((2-(3-carbomethoxyphenyl)-2-hydroxyethyl)amino)butyl)-1,3-benzodioxole-2,2-dicarboxylic acid, dimethyl ester |
| 58 | 5-(2-((2-(3-carbomethoxyphenyl)-2-hydroxyethyl)amino)butyl)-1,3-benzodioxole-2,2-dicarboxylic acid, dibutyl ester |
| 59 | 5-(2-((2-(3-methylthiophenyl)-2-hydroxyethyl)amino)propyl)-1,3-benzodioxole-2,2-dicarboxylic acid, dimethyl ester |
| 60 | 5-(2-((2-(3-carbomethoxyphenyl)-2-hydroxyethyl)amino)propyl)-1,3-benzodioxole-2,2-dicarboxylic acid, diethyl ester |
| 61 | 5-(2-((2-(3-methylthiophenyl)-2-hydroxyethyl)amino)propyl)-1,3-benzodioxole-2,2-dicarboxylic acid, diethyl ester |
| 62 | 5-(2-((2-(3-methylthiophenyl)-2-hydroxyethyl)amino)propyl)-1,3-benzodioxole-2,2-dicarboxylic acid, dibutyl ester |
| 63 | 5-(2-((2-(3-methylthiophenyl)-2-hydroxyethyl)amino)butyl)-1,3-benzodioxole-2,2-dicarboxylic acid, dimethyl ester |
| 64 | 5-(2-((2-(3-methylthiophenyl)-2-hydroxyethyl)amino)butyl)-1,3-benzodioxole-2,2-dicarboxylic acid, diethyl ester |
| 65 | 5-(2-((2-(3-methylthio-4-chlorophenyl)-2-hydroxyethyl)amino)butyl)-1,3-benzodioxole-2,2-dicarboxylic acid, dibutyl ester |
| 66 | 5-(2-((2-(3-cyanophenyl)-2-hydroxyethyl)amino)propyl)-1,3-benzodioxole-2,2-dicarboxylic acid, dimethyl ester |
| 67 | 5-(2-((2-(3-cyanophenyl)-2-hydroxyethyl)amino)propyl)-1,3-benzodioxole-2,2-dicarboxylic acid, diethyl ester |
| 68 | 5-(2-((2-(3-cyanophenyl)-2-hydroxyethyl)amino)propyl)-1,3-benzodioxole-2,2-dicarboxylic acid, dibutyl ester |
| 69 | 5-(2-((2-(3-cyanophenyl)-2-hydroxyethyl)amino)butyl)-1,3-benzodioxole-2,2-dicarboxylic acid, dimethyl ester |
| 70 | 5-(2-((2-(3-cyanophenyl)-2-hydroxyethyl)amino)butyl)-1,3-benzodioxole-2,2-dicarboxylic acid, diethyl ester |
| 71 | 5-(2-((2-(3-cyanophenyl)-2-hydroxyethyl)amino)butyl)-1,3-benzodioxole-2,2-dicarboxylic acid, dibutyl ester |
| 72 | 5-(2-((2-(2-chlorophenyl)-2-hydroxyethyl)amino)propyl)-1,3-benzodioxole-2,2-dicarboxylic acid, dimethyl ester |
| 73 | 5-(2-((2-(2-chlorophenyl)-2-hydroxyethyl)amino)propyl)-1,3-benzodioxole-2,2-dicarboxylic acid, diethyl ester |
| 74 | 5-(2-((2-(2-bromophenyl)-2-hydroxyethyl)amino)propyl)-1,3-bezodioxole-2,2-dicarboxylic acid, dimethyl ester |
| 75 | 5-(2-((2-(2-bromophenyl)-2-hydroxyethyl)amino)propyl)-1,3-bezodioxole-2,2-dicarboxylic acid, dipropyl ester |
| 76 | 5-(2-((2-(2-fluorophenyl-2-hydroxyethyl)amino)propyl)-1,3-benzodioxole-2,2-dicarboxylic acid, dimethyl ester |
| 77 | 5-(2-((2-(2-fluorophenyl)-2-hydroxyethyl)amino)propyl)-1,3-bezodioxole-2,2-dicarboxylic acid, diethyl ester |

TABLE A-continued

| EXAMPLE | COMPOUND |
|---|---|
| 78 | 5-(2-((2-(2-trifluoromethylphenyl)-2-hydroxyethyl)amino)propyl)-1,3-benzodioxole-2,2-dicarboxylic acid, dimethyl ester |
| 79 | 5-(2-((2-(2-trifluoromethylphenyl)-2-hydroxyethyl)amino)propyl)-1,3-benzodioxole-2,2-dicarboxylic acid, diethyl ester |
| 80 | 5-(2-((2-(2-methoxyphenyl)-2-hydroxyethyl)amino)propyl)-1,3-benzodioxole-2,2-dicarboxylic acid, dimethyl ester |
| 81 | 5-(2-((2-(2-methoxyphenyl)-2-hydroxyethyl)amino)propyl)-1,3-benzodioxole-2,2-dicarboxylic acid, diethyl ester |
| 82 | 5-(2-((2-(2-methoxyphenyl)-2-hydroxyethyl)amino)propyl)-1,3-benzodioxole-2,2-dicarboxylic acid, dimethyl ester |
| 83 | 5-(2-((2-(2-methoxyphenyl)-2-hydroxyethyl)amino)propyl)-1,3-benzodioxole-2,2-dicarboxylic acid, diethyl ester |
| 84 | 5-(2-((2-(2-dimethylaminophenyl)-2-hydroxyethyl)amino)propyl)-1,3-benzodioxole-2,2-dicarboxylic acid, dimethyl ester |
| 85 | 5-(2-((2-(2-dimethylaminophenyl)-2-hydroxyethyl)amino)propyl)-1,3-benzodioxole-2,2-dicarboxylic acid, diethyl ester |
| 86 | 5-(2-((2-(2-methylthiophenyl)-2-hydroxyethyl)amino)propyl)-1,3-benzodioxole-2,2-dicarboxylic acid, dimethyl ester |
| 87 | 5-(2-((2-(2-methylthiophenyl)-2-hydroxyethyl)amino)propyl)-1,3-benzodioxole-2,2-dicarboxylic acid, diethyl ester |
| 88 | 5-(2-((2-(2-ethoxyphenyl)-2-hydroxyethyl)amino)propyl)-1,3-benzodioxole-2,2-dicarboxylic acid, dimethyl ester |
| 89 | 5-(2-((2-ethoxy-3-chlorophenyl)-2-hydroxyethyl)amino)propyl)-1,3-benzodioxole-2,2-dicarboxylic acid, diethyl ester |
| 90 | 5-(2-((2-(4-chlorophenyl)-2-hydroxyethyl)amino)propyl)-1,3-benzodioxole-2,2-dicarboxylic acid, dimethyl ester |
| 91 | 5-(2-((2-(4-chlorophenyl)-2-hydroxyethyl)amino)butyl)-1,3-benzodioxole-2,2-dicarboxylic acid, dimethyl ester |
| 92 | 5-(2-((2-(4-iodophenyl)-2-hydroxyethyl)amino)propyl)-1,3-benzodioxole-2,2-dicarboxylic acid, dimethyl ester |
| 93 | 5-(2-((2-(4-iodophenyl)-2-hydroxyethyl)amino)butyl)-1,3-benzodioxole-2,2-dicarboxylic acid, dimethyl ester |
| 94 | 5-(2-((2-(4-fluorophenyl)-2-hydroxyethyl)amino)propyl)-1,3-benzodioxole-2,2-dicarboxylic acid, dimethyl ester |
| 95 | 5-(2-((2-(4-fluorophenyl)-2-hydroxyethyl)amino)butyl)-1,3-benzodioxole-2,2-dicarboxylic acid, dimethyl ester |
| 96 | 5-(2-((2-(4-trifluoromethylphenyl)-2-hydroxyethyl)amino)propyl)-1,3-benzodioxole-2,2-di-carboxylic acid, dimethyl ester |
| 97 | 5-(2-((2-(4-trifluoromethylphenyl)-2-hydroxyethyl)amino)butyl)-1,3-benzodioxole-2,2-di-carboxylic acid, dimethyl ester |
| 98 | 5-(2-((2-(4-methoxyphenyl)-2-hydroxyethyl)amino)propyl)-1,3-benzodioxole-2,2 dicarboxylic acid, dimethyl ester |
| 99 | 5-(2-((2-(4-methoxyphenyl)-2-hydroxyethyl)amino)butyl)-1,3-benzodioxole-2,2 dicarboxylic acid, dimethyl ester |
| 100 | 5-(2-((2-(4-ethylphenyl)-2-hydroxyethyl)amino)propyl)-1,3-benzodioxole-2,2 dicarboxylic acid, dimethyl ester |
| 101 | 5-(2-((2-(4-ethylphenyl)-2-hydroxyethyl)amino)butyl)-1,3-benzodioxole-2,2 dicarboxylic acid, dimethyl ester |
| 102 | 5-(2-((2-(4-dimethylaminophenyl)-2-hydroxyethyl)amino)propyl)-1,3-benzodioxole-2,2 dicarboxylic acid, dimethyl ester |
| 103 | 5-(2-((2-(4-dimethylaminophenyl)-2-hydroxyethyl)amino)butyl)-1,3-benzodioxole-2,2 dicarboxylic acid, dimethyl ester |
| 104 | 5-(2-((2-(4-methylthiophenyl)-2-hydroxyethyl)amino)propyl)-1,3-benzodioxole-2,2 dicarboxylic acid, dimethyl ester |
| 105 | 5-(2-((2-(4-methylthiophenyl)-2-hydroxyethyl)amino)butyl)-1,3-benzodioxole-2,2 dicarboxylic acid, dimethyl ester |
| 106 | 5-(2-((2-(4-cyanophenyl)-2-hydroxyethyl)amino)propyl)-1,3-benzodioxole-2,2-dicarboxylic acid, dimethyl ester |
| 107 | 5-(2-((2-(4-cyanophenyl)-2-hydroxyethyl)amino)butyl)-1,3-benzodioxole-2,2-dicarboxylic acid, dimethyl ester |

The above mentioned patents and publications are incorporated herein by reference.

Many variations of the present invention will suggest themselves to those who are skilled in the art in light of the above detailed description. All such obvious modifications are within the full intended scope of the appended claims

We claim:

1. A method of increasing the content of lean meat in edible animals which comprises administering to an edible animal an effective amount of a compound of the formula

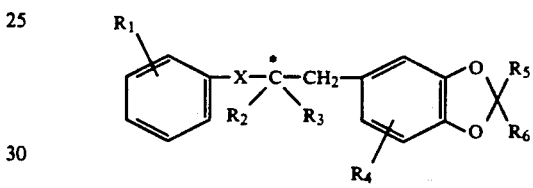

wherein $R_1$ and $R_4$ may be one or more groups which may be the same or different and are selected from the group consisting of hydrogen, $C_1$ to $C_4$ alkyl, $C_1$ to $C_4$ alkoxy, hydroxy, halogen, trifluoromethyl, carboxy, hydroxyalkyl, alkoxycarbonyl, $C_1$ to $C_4$ thioalkyl, sulfonyl and sulfinyl; X is a divalent radical consisting of

wherein R' is selected from the group consisting of hydrogen, $C_1$ to $C_4$ alkyl and $C_1$ to $C_4$ acyl; $R_2$ and $R_3$ may be the same or differenct and are selected from the group consisting of hydrogen and $C_1$ $C_4$ alkyl; $R_5$ and $R_6$ are selected from the group consisting of hydrogen, carboxy, alkoxycarbonyl, hydroxymethyl, $-CH_2OCH_2COOR_7$ and $-CH_2OCH_2CH_2OR_7$ where $R_7$ is hydrogen or $C_1$ to $C_4$ alkyl; except that $R_5$ and $R_6$ may not both be hydrogen; the asterisks denote asymmetric carbon atoms; or a pharmaceutically acceptable salt or ester thereof, the enantiomers thereof, the racemic mixtures thereof and the diastereomeric mixtures thereof.

2. A method according to claim 1 wherein $R_1$ of the compound is one or two of the groups as defined.

3. A method according to claim 2 wherein the compound is 1,3-Benzodioxole-2,2-dicarboxylic acid, 5-[2-[[2-(3-chlorophenyl)-2-hydroxyethyl]amino]propyl]-, disodium salt (R*,R*)-(+/−).

4. A method according to claim 2 wherein the compound is 1,3-Benzodioxole-2,2=dicarboxylic acid, 5-[2-[[2-(3-chlorophenyl)-2-hydroxyethyl]amino]propyl]-, dimethyl ester, hydrobromide,(R*,R*)-(+/−).

5. A method according to claim 2 wherein the compound is 1,3-Benzodioxole-2,2-dicarboxylic acid, 5-[2-[[2-(3-chlorophenyl)-2-hydroxyethyl]amino]propyl]-, disodium salt,[R-(R*,R*)].

6. A method according to claim 2 wherein the compound if 1,3-Benzodioxole-2,2-dicarboxylic acid, 5-[2-[[2-(3-chlorophenyl)-2-hydroxyethyl]amino]propyl]-, bis(1-methylethyl) ester, hydrochloride, [R-(R*,R*)].

* * * * *